United States Patent
Märkl et al.

(10) Patent No.: US 6,197,729 B1
(45) Date of Patent: Mar. 6, 2001

(54) SUBSTITUTED CYCLOHEXYLAMINOPYRIMIDINES

(75) Inventors: Martin Märkl, Frankfurt; Wolfgang Schaper, Diedorf; Oswald Ort, Glashütten; Harald Jakobi, Frankfurt; Ralf Braun, Büttelborn; Gerhard Krautstrunk, Bad Vilbel; Ulrich Sanft, Eppstein/Ts.; Werner Bonin, Kelkheim; Herbert Stark, Kelkheim; Sergej Pasenok, Kelkheim; Ivan Cabrera, Dreieich, all of (DE)

(73) Assignee: Hoechst Schering Agrevo, Berlin (DE)

( * ) Notice: Subject to any disclaimer, the term of this patent is extended or adjusted under 35 U.S.C. 154(b) by 0 days.

(21) Appl. No.: 09/363,721

(22) Filed: Jul. 29, 1999

(30) Foreign Application Priority Data

Aug. 1, 1998 (GB) .................................... 9816729

(51) Int. Cl.⁷ .................. A01N 43/54; C07D 239/86; C07D 239/94
(52) U.S. Cl. .................. 504/239; 504/239; 504/240; 504/242; 504/243; 544/293; 544/319; 544/326; 544/329
(58) Field of Search ................... 514/256, 259, 514/269; 544/293, 319, 326, 329; 504/239, 240, 242, 243

(56) References Cited

U.S. PATENT DOCUMENTS

| | | | |
|---|---|---|---|
| 5,571,815 | * 11/1996 | Schaper et al. | 514/269 |
| 5,691,321 | * 11/1997 | Schaper et al. | 514/63 |
| 5,723,450 | 3/1998 | Reuschling et al. | 514/63 |
| 5,730,973 | 3/1998 | Morales et al. | 424/93.5 |
| 6,107,299 | * 8/2000 | Jakobi et al. | 514/256 |

FOREIGN PATENT DOCUMENTS

| | | |
|---|---|---|
| 0370391 | 5/1990 | (EP) . |
| 0470600 | 2/1992 | (EP) . |

OTHER PUBLICATIONS

Takao Sakamoto et al., "Condensed Heteroaromatic Ring Systems, VII." Chemical and Pharmceutical Bulletin, vol. 34, No. 7, 1986. pp. 2719–2724, XP002126073.
Derwent Abstract of WO 96/11913, (1996).

* cited by examiner

Primary Examiner—Mukund J. Shah
Assistant Examiner—Ben Schroeder
(74) Attorney, Agent, or Firm—Frommer Lawrence & Haug LLP

(57) ABSTRACT

Compounds of formula I

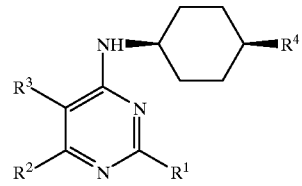

where
$R^1$ is hydrogen, chlorine, fluorine or methyl,
$R^2$ and $R^3$, which may be the same or different from each other, are hydrogen, halogen, cyano, $(C_1-C_4)$-alkyl, vinyl, ethynyl, $(C_1-C_4)$-alkoxy, $(C_1-C_4)$-alkoxy-$(C_1-C_4)$-alkyl, fluorovinyl or fluoroethyl, or
$R^2$ and $R^3$ together with the linking carbon atoms form a benzo ring, and
$R^4$ is $(C_2-C_4)$-alkyl, $(C_2-C_4)$-alkenyl or $(C_3-C_4)$-alkinyl, each of which is substituted by at least two fluorine atoms and optionally substituted by $C_{1-4}$-alkoxy, cyanomethoxy, $(C_3-C_4)$-alkenyloxy or $(C_3-C_4)$-alkinyloxy, are useful as pesticides, especially against insects, acarids and fungi. The invention includes a novel process for fluorinating certain pyrimidines.

10 Claims, No Drawings

SUBSTITUTED CYCLOHEXYLAMINOPYRIMIDINES

The invention relates to new substituted cyclohexylaminopyrimidines and their use as pesticides, especially insecticides and acaricides.

In our WO 93/19050, we have described pyrimidines inter alia substituted in the 4-position by cycloalkylamino. One substituent described on the cyclohexyl group is haloalkyl. However no compounds are exemplified in this application with such substituents and especially no compounds are disclosed with a fluoroalkyl substituent.

In our WO 9611913 we have disclosed other 4-cyclohexylaminopyrimidines, in which the cyclohexyl can be substituted by various substituted alkyl groups. Only three such compounds are disclosed carrying a fluorinated alkyl group. two of these carry an extra substituent, namely hydroxy and cyclohexyl respectively and the third group is isopropyl substituted by only one fluorine.

We have now found that certain fluoroalkyl-substituted cyclohexylamino compounds have especially valuable properties.

Thus the invention provides the use as pesticides of compounds of formula I

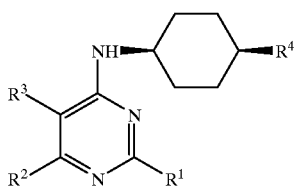

(I)

where $R^1$ is hydrogen, chlorine, fluorine or methyl, $R^2$ and $R^3$, which may be the same or different from each other, are hydrogen, halogen, cyano, $(C_1-C_4)$-alkyl, vinyl, ethynyl, $(C_1-C_4)$-alkoxy, $(C_1-C_4)$-alkoxy-$(C_1-C_4)$-alkyl, fluorovinyl or fluoroethyl, or $R^2$ and $R^3$ together with the linking carbon atoms form a benzo ring, and $R^4$ is $(C_2-C_4)$-alkyl, $(C_2-C_4)$-alkenyl or $(C_3-C_4)$-alkinyl, each of which is substituted by at least two fluorine atoms and optionally substituted by $C_{1-4}$-alkoxy, cyanomethoxy, $(C_3-C_4)$-alkenyloxy or $(C_3-C_4)$-alkynyloxy, and acid addition salts.

Most of the compounds of formula I are novel and the invention includes compounds of formula I as defined above with the proviso that $R^4$ is not 3,3,3-trifluoropropyl or 2,2,2-trifluoro-1-methylethyl when $R^2$ is ethyl and $R^3$ is chloro; and $R^4$ is not 2,2,2-trifluoro-1-methylethyl when $R^2$ is methyl and $R^3$ is chloro or bromo.

It generally preferred that $R^1$ is hydrogen, $R^2$ is $(C_1-C_4)$-alkyl, especially ethyl or methoxymethyl, $R^3$ is preferably hydrogen, methoxy, ethynyl or halogen, especially chlorine or fluorine.

$R^4$ preferably includes a trifluoromethyl group. Particularly preferred groups for $R^4$ are 3,3,3-trifluoropropyl or 2,2,2-trifluoro-1-methylethyl.

The present invention relates to the compounds of the formula I in the form of the free base or an acid addition salt. Acids which can be used for salt formation are inorganic acids, such as hydrochloric acid, hydrobromic acid, nitric acid, sulfuric acid, phosphoric acid, or organic adds, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

In the compounds of the invention, the NH and $R^4$ are in a cis configuration. The compounds may contain one or more asymmetric carbon atoms or stereoisomeric producing double bonds. Enantiomers or diastereomers can therefore occur. The invention relates both to pure isomers and to mixtures thereof. The mixtures of diastereomers can be separated into the components by customary methods, for example by selective crystallisation from suitable solvents or by chromatography. Racemates can be separated into the enantiomers by customary methods, thus, for example, by salt formation with a chiral, enantiomerically pure acid, separation of the diastereomeric salts and liberation of the pure enantiomers by means of a base.

The compounds of formula I may be prepared in known manner, for example by reacting a compound of formula II

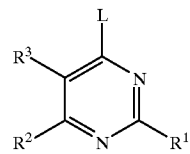

(II)

where $R^1$, $R^2$ and $R^3$ are as defined under formula I and L is a leaving group, for example halogen, alkylthio, alkanesulfonyloxy, arylsulfonyloxy, alkylsulfonyl or arylsulfonyl, with a nucleophile of formula III

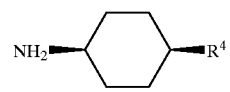

(III)

where $R^4$ is as defined above under formula I, and, if desired, converting the compound of the formula I obtained in this manner or in another manner into its acid addition salt.

The leaving group L can be varied within wide limits and can be, for example, halogen, such as fluorine, chlorine, bromine or iodine; alkylthio, such as methyl- or ethylthio; alkylsulfonyloxy, such as methane-, trifluoromethyl- or ethylsulfonyloxy; arylsulfonyloxy, such as benzenesulfonyloxy; or toluenesulfonyloxy, alkylsulfonyl such as methyl- or ethylsulfonyl; or arylsulfonyl such as phenyl- or tolylsulfonyl.

The abovementioned reaction is generally carried out in a temperature range from 20–150° C., advantageously in the presence of a base and, if appropriate, in an inert organic solvent such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. It is also possible to employ mixtures of these solvents.

Suitable bases are, for example, alkali metal or alkaline earth metal carbonates, bicarbonates, hydroxides, amides or hydrides, such as sodium carbonate, sodium bicarbonate, potassium carbonate, sodium hydroxide, sodium amide or sodium hydride, or organic bases, such as triethylamine or pyridine, or a second equivalent of the nucleophile of formula III.

The compounds of the formula II are in most cases known from the literature or can be prepared by methods similar to those that are known (cf. EP-A-370 391, EP-A-470 600, DE-A-43 31 179, DE-A-44 04 702).

The nucleophiles of the formula III can be prepared by known processes, for example by reducing an oxime or an azide with a suitable reducing agent, for example a complex metal hydride or hydrogen in the presence of a hydrogenation catalyst, reductive amination or Leuckart-Wallach reaction of a ketone or Gabriel reaction of an alkyl halide or alkyl tosylate.

A method suitable for preparing the cyclohexylamines of formula III, is the reductive amination of appropriately substituted cyclohexanones with ammonium salts and sodium cyanoborohydride or with ammonium and hydrogen in the presence of metal catalysts such as nickel, ruthenium, rhodium or palladium, the proportion of the desired cis-amine being particularly high with this method.

A further method is the hydrogenation of anilines or aromatic nitro compounds in the presence of hydrogenation catalysts.

Some suitably substituted cyclohexanone intermediates are known from the literature, or they can be prepared by known synthesis processes. Such processes are, for example:

a) hydrogenation of the phenol ring and oxidation of the resulting cyclohexanol, the fluorine-containing radical $R^4$ being synthesised by standard processes.

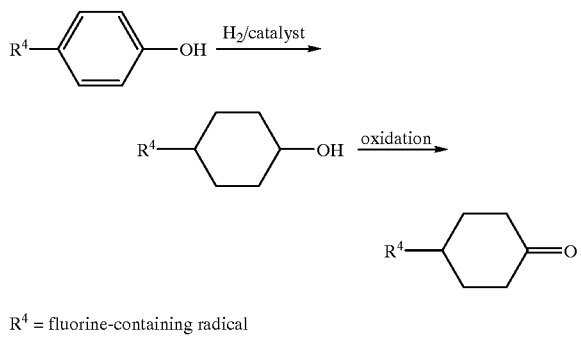

$R^4$ = fluorine-containing radical b) derivatisation of a mono-protected cyclohexane-1,4-dione:

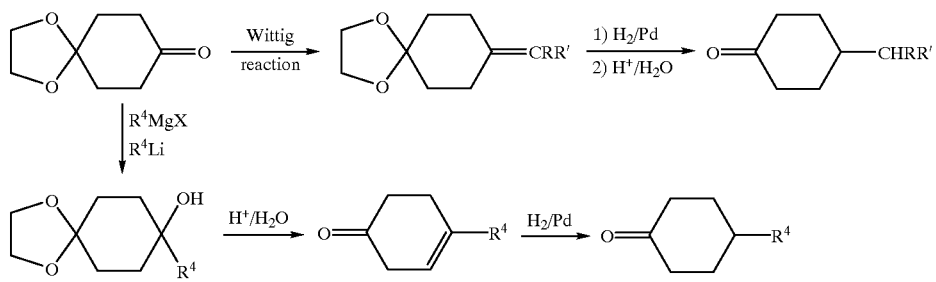

At least of R, $R^1$ or $R^4$ contains fluorine.

c) derivatisation of a protected cyclohexanone

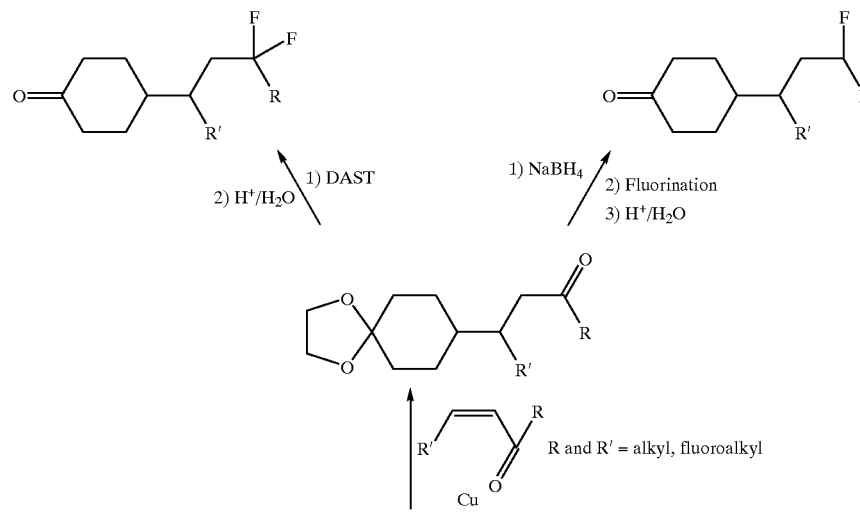

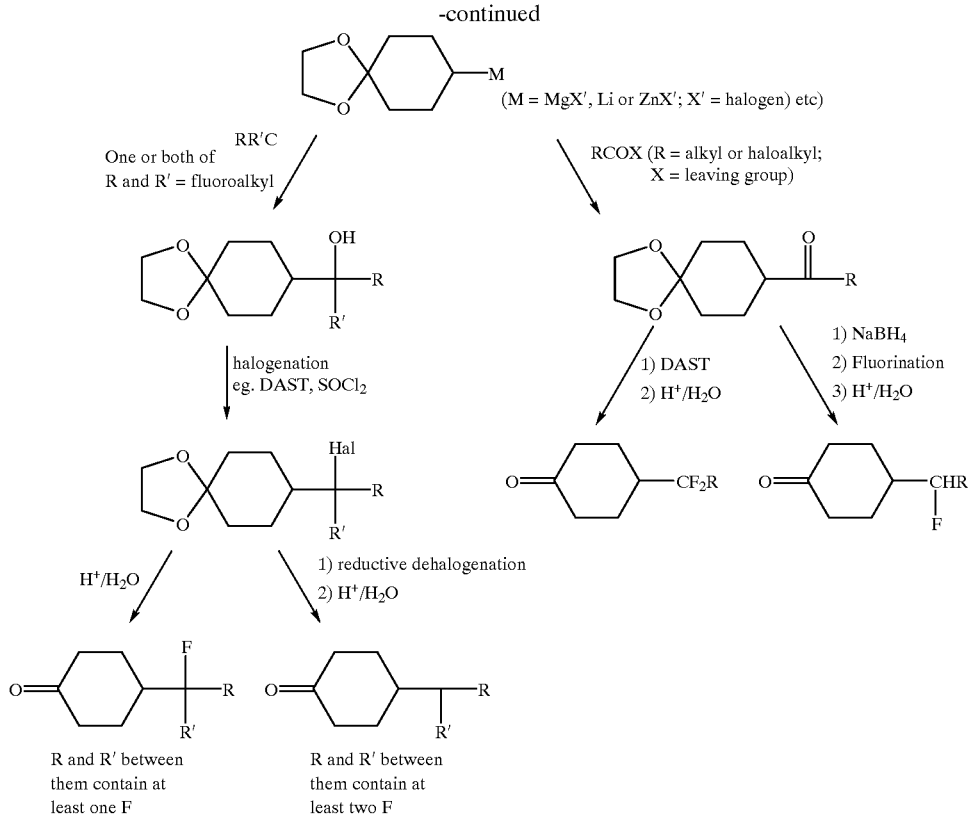
Further processes:
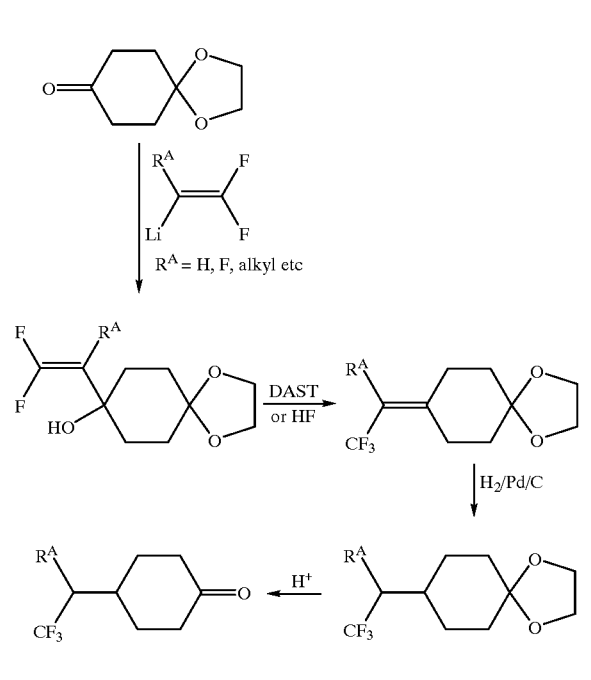
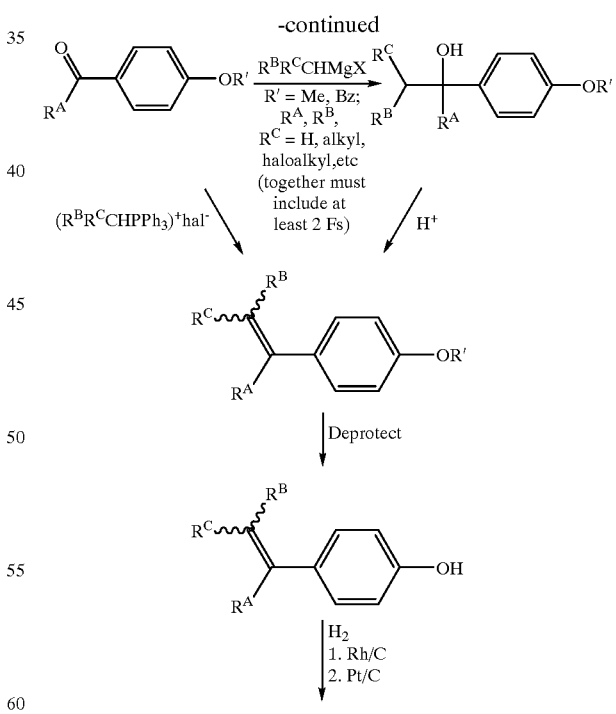

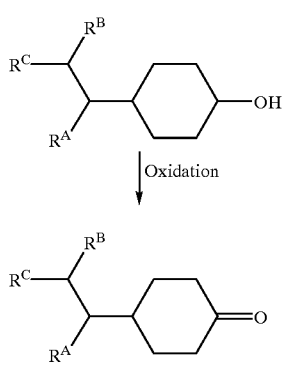

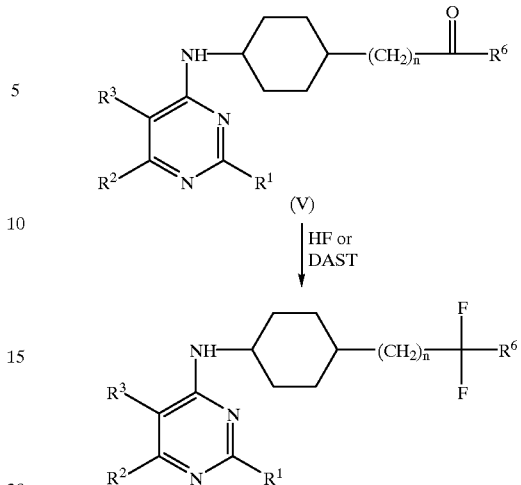

Some of the reactions described above can in principle also be carried out on heterocycle precursors of the formulae IV (cf. DE-A-4331178).

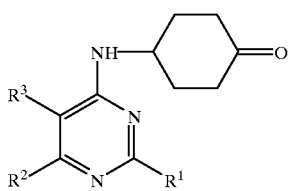

(IV)

Further possibilities for synthesising the final products of the formula I are the application of known halogenating reactions on appropriate heterocycle precursors, such as, for example, the conversion of alcohol derivatives into halogen-containing radicals $R^4$; for example

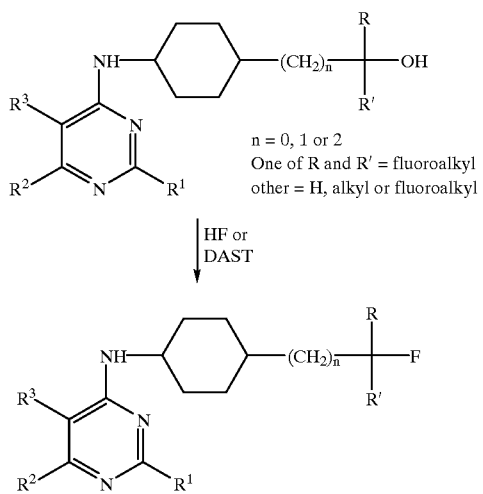

n = 0, 1 or 2
One of R and R' = fluoroalkyl
other = H, alkyl or fluoroalkyl

Aldehydes and ketones of formula V, where $R^6$ is hydrogen or $C_{1-6}$-alkyl and n is 1 to 3, can be fluorinated to give compounds of the invention as follows.

The compounds of formula V, which are novel, can be prepared for example by oxidising the appropriate alcohols. In the case of the aldehydes ($R^6$=HO, the alcohols can be obtained by reduction of the corresponding ester. These intermediates are also novel. The invention thus includes compounds of formula VI

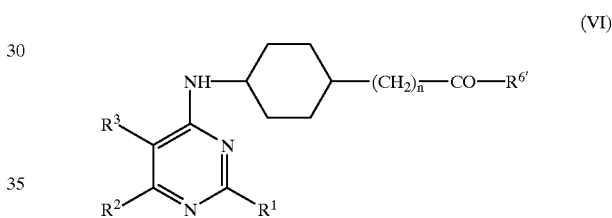

(VI)

where $R^{6'}$ is hydrogen or $C_{1-6}$-alkyl and n is 1 to 3.

Collections of compounds of the formula (I) which can be synthesised by the schemes above, may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as it is described, for example, by S. H. DeWitt in "Annual Reports in Combinatorial Chemistry and Molecular Diversity: Automated synthesis", Volume 1, Verlag Escom 1997, pages 69 to 77.

A series of commercially available apparatuses as they are offered by, for example, Stem Corporation, Woodrolfe Road, Tollesbury, Essex, CM9 8SE, England or H+P Labortechnik GmbH, Bruckmannring 28, 85764 Oberschleißheim, Germany, may be used for the parallel procedure of the reaction and work-up. For the parallel purification of compounds of the formula (I), or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula (I) in the form of substance collections which are termed libraries. The present invention also relates to libraries which comprise at least two compounds of the formula (I).

Compounds where $R^3$ is fluorine can be obtained by direct fluorination of compounds of formula I where $R^3$ is hydrogen. This is novel process for the preparation 4-amino-5-fluoropyrimidines and the invention thus includes a process for the preparation of fluoropyrimidines of formula X

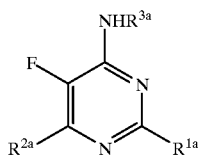

(X)

where $R^{1a}$ is hydrogen, $(C_1–C_4)$-alkyl, preferably methyl, $(C_1–C_4)$-haloalkyl, preferably mono-, di- or trifluoromethyl or halogen, preferably fluorine or chlorine, $R^{2a}$ is $(C_1–C_4)$-alkyl, preferably methyl or ethyl, $(C_1–C_4)$-alkoxy-$(C_1–C_4)$-alkyl, preferably methoxymethyl or $(C_1–C_4)$-haloalkyl, preferably fluoromethyl or fluoroethyl and $R^{3a}$ is a $(C_1–C_{20})$-alkyl or $(C_3–C_8)$-cycloalkyl, both of which are optionally substituted and in which, so far as it is chemically feasible, one or two carbon units may be replaced by oxygen or a group $S(O)_x$, where x=0, 1 or 2, which comprises fluorinating in position 5, a compound of the formula XI

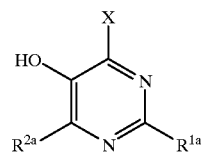

(XI)

where X is OH or $NHR^{3a}$ and $R^{1a}$, $R^{2a}$ and $R^{3a}$ have the meanings given above for formula I to give a compound of the formula I or II and, if X is OH, converting the resulting compound, in known manner, into a compound of formula X.

When X is OH, the process according to the invention, is carried out by fluorinating the compound of formula XI, electrophilically, in position 5 of the pyrimidine and converting the resulting compound, after conversion of the hydroxy group in position 4 of the pyrimidine into a leaving group (for example by chlorination with phosphorus oxychloride) and subsequent reaction with an amine of the formula $R^{3a}NH_2$, in which $R^{3a}$ has the meanings given for formula X, in the presence of a base to give the end products of the formula X. Suitable fluorinating agents are electrophilic fluorinating agents or else elemental fluorine. Electrophilic fluorinating agents are, for example N-fluoropyridinium derivatives, such as N-fluoropyridinium triflate, N-fluoro-2,4,6-trimethylpyridinium triflate, N-fluoro-2,6-dichloropyridinium triflate, N-fluoro-3,5-dichloropyridinium triflate or N-fluoropentachloropyridinium triflate or N-fluorosulfonamide or sulfonimide derivatives, such as, for example N-fluoro-tert-butyl-p-toluenesulfonamide, N-fluorotrifluoromethylsulfonimide, N-fluorobenzenesulfonimide (NFSI), N-fluoro-o-benzenedisulfonimide, 2-fluoro-3,3-dimethyl-2,3-dihydro-1,2-benzisothiazole 1,1-dioxide, or N-fluorooxathiazinone dioxides, such as, for example benz-1,2,3-oxathiazine-4 (3F)-one 2,2-dioxide or N-fluoroammonium derivatives, such as, for example N-fluoroquinuclidinium triflate, 1-hydroxy-4-fluoro-1,4-diazabicyclo[2,2,2]octane bis-tetrafluoroborate (Accufluor®), 1-chloromethyl-4-fluoro-1,4-diazabicyclo[2.2.2]octane bis-tetrafluoroborate (F-TEDA-$BF_4$, Selectfluor®), but also perchloryl fluoride, trifluoromethyl hypofluorite, caesium fluorooxysulfate or xenon difluoride.

Fluorination with elemental fluorine is here advantageously carried out by introducing gaseous fluorine, in equimolar amounts or in excess, preferably in equimolar amounts or up to twice the molar amount, preferably as a mixture with an inert carrier gas such as nitrogen or helium, into a solution of the compound of the formula III in an inert organic solvent, such as, for example acetic add, Frigen®11 or preferably formic acid or trifluoroacetic acid and allowing it to react at a temperature between –10° C. and 30° C., preferably between –5° C. and 15° C. Fluorination with F-TEDA-$BF_4$ is advantageously carried out by reacting F-TEDA-$BF_4$ and a compound of formula III in an inert solvent such as, for example water, dimethylformamide, diethyl ether, tetrahydrofuran or acetonitrile or else in a mixture of these solvents, in a temperature range between 0° C. and 80° C., preferably between +10° C. and 40° C.

If X is $NHR^{3a}$, the process according to the invention is carried out, for example by converting a compound of the formula XI (X=OH) after conversion of the hydroxyl group in position 4 of the pyrimidine into a leaving group (for example by chlorination with phosphorus oxychloride) and subsequent reaction, with a secondary amine of the formula $R^{3a}NH_2$, in the presence of a base into a compound of the formula XI ($X=NHR^{3a}$), and then fluorinating this compound electrophilically in position 5 of the pyrimidine. The fluorinating reagents and reaction conditions correspond to those mentioned above.

While being tolerated well by plants and having favourable toxicity toward warm-blooded animals, the active substances of formula I are suitable for controlling animal pests, especially insects, arachnids, helminths and molluscs, and very particularly preferably for controlling insects and acarids, which are encountered in agriculture, in animal breeding, in forestry, in the protection of stored products and materials, and in the hygiene sector. They are active against normally sensitive and resistant species and against some or even all stages of development. The abovementioned pests include:

From the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the isopoda, for example *Oniscus asselus, Armadium vulgar* and *Porcellio scaber.*

From the order of the Diplopoda, for example *Blaniulus guttulatus.*

From the order of the Chilopoda, for example *Geophilus carpophagus* and Scutigera spp.

From the order of the Symphyla, for example *Scutigerella immaculata.*

From the order of the Thysanura, for example *Lepisma saccharina.*

From the order of the Collembola, for example *Onychiurus armatus.*

From the order of the Orthoptera, for example *Blatta orientalis, Periplaneta americana, Leucophaea madeirae, Blatella germanica, Acheta domesticus,* Gryllotalpa spp., *Locusta migratoria migratorioides, Melanoplus differentialis* and *Schistocerca gregaria.*

From the order of the isoptera, for example Reticulitermes spp.

From the order of the Anoplura, for example *Phylloera vastatrix*, Pemphigus spp., *Pediculus humanus corporis*, Haematopinus spp. and Linognathus spp.

From the order of the Mallophaga, for example Trichodecte spp. and Damalinea spp.

From the order of the Thysanoptera, for example *Hercinothrips femoralis, Thrips tabaci* and Frankliniella spp.

From the order of the heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum,* Aphis spp., *Brevicoryne brassicae, Cryptomyzus ribis, Doralis fabae, Doralis pomi, Eriosoma lanigerum, Hyalopterus arandinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortix viridana,* Cuaphalocrocis spp. and Manduca spp.

From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrynchus assimilis, Hypera postica,* Dermestes spp., Trogorma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conorus spp., *Melolontha melolontha, Amphimallon solstitialis, Costelytra zealandica* and Lissorhoptus spp.

From the order of the Hymenoptera, for example Diprion spp., Hoplocampa spp., Lasius spp., *Monomorium pharaonis* and Vespa spp.

From the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hyporma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example *Xenopsylla cheopsis* and Ceratophyllus spp.

From the order of the Arachnida, for example *Scorpio maurus* and *Latrodectus mactans.*

From the class of the helminths, for example Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the Gastropoda, for example, Deroceras spp., Arion spp., Lymnaea spp., Galba spp., Succinea spp., Biomphalaria spp., Bulinus spp. and Oncomelania spp.

From the class of the Bivalva, for example Dreissena spp.

The plant-parasitic nematodes which can be controlled in accordance with the invention include, for example, the root-parasitic soil nematodes such as, for example, those of the genera Meloidogyne (root-knot nematodes, such as *Meloidogyne incognita, Meloidogyne hapla* and *Meloidogyne javanica*), heterora and Globora (cyst-forming nematodes, such as *Globora rostochiensis, Globora pallida, heterora trifolii*) and of the genera Radopholus (such as *Radopholus similis*), Pratylenchus (such as *Pratylenchus neglectus, Pratylenchus penetrans* and *Pratylenchus curvitatus*), Tylenchulus (such as *Tylenchulus semipenetrans*), Tylenchorhynchus (such as *Tylenchorhynchus dubius* and *Tylenchorhynchus claytoni*), Rotylenchus (such as *Rotylenchus robustus*), Helicotylenchus (such as *Helicotylenchus multicinctus*), Belonoaimus (such as *Belonoaimus longicaudatus*), Longidorus (such as *Longidorus elongatus*), Trichodorus (such as *Trichodorus primitivus*) and Xiphinema (such as *Xiphinema index*).

The compounds according to the invention can also be used to control the nematode genera Ditylenchus (stem parasites, such as *Ditylenchus dipsaci* and *Ditylenchus destriuctor*), Aphelenchoides (leaf nematodes, such as *Aphelenchoides ritzemabosi*) and Anguina (leaf-gall nematodes, such as *Anguina tritici*).

The invention also relates to compositions, especially insecticidal and acaricidal compositions, which comprise the compounds of the formula I in addition to suitable formulation auxiliaries.

The compositions according to the invention comprise the active substances of the formulae I in general in a proportion of from 1 to 95% by weight. They can be formulated in various ways depending on the biological and/or chemico-physical parameters which prevail. Possible formulations which are suitable are therefore: wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th ed. 1986; van Falkenberg, "Pesticides formulations", Marcel Dekker N.Y., 2nd ed. 1972–73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; Marsden, "Solvents Guide", 2nd ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie", Volume 7, C. Hauser Verlag Munich, 4th ed. 1986.

Based on these formulations, it is also possible to produce combinations with other pesticidally active substances, fertilisers and/or growth regulators, for example in the form of a ready-mix or a tank mix. Wettable powders are preparations, uniformly dispersible in water, which contain, beside the active substance and in addition to a diluent or inert material, wetting agents, for example polyoxyethylated alkylphenols, polyoxyethylated fatty alcohols, alkyl- or alkylphenolsulfonates, and dispersing agents, for example sodium ligninsulfonate or sodium 2,2'-dinaphthylmethane-6,6'-disulfonate. Emulsifiable concentrates are prepared by dissolving the active substance in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylarylsulfonates, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite, pyrophillite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or alternatively mineral oils. Suitable active substances can also be granulated in the fashion conventional for the preparation of fertilizer granules, if desired as a mixture with fertilisers.

In wettable powders, the concentration of active substance is, for example, from approximately 10 to 90% by weight, the remainder to 100% by weight being composed of customary formulation components. In the case of emulsifiable concentrates, the concentration of active substance may be from approximately 5 to 80% by weight. Dust formulations comprise in most cases from 5 to 20% by weight of active substance, sprayable solutions from about 2 to 20% by weight. In the case of granules, the content of active substance depends partly on whether the active compound is in liquid or solid form and on which granulation auxiliaries, fillers, etc. are being used.

In addition, the abovementioned formulations of active substance comprise, if appropriate, the adhesives, wetting agents, dispersants, emulsifiers, penetrants, solvents, fillers or carriers which are customary in each case.

The concentrates, which are in the commercially customary form, are if appropriate diluted in the customary manner for their use, for example using water in the case of wettable powders, emulsifiable concentrates, dispersions and some microgranules. Dust and granule preparations, and also sprayable solutions, are normally not diluted any further with other inert substances before being used.

The application rate required varies with the external conditions, such as temperature and humidity among others. It can fluctuate within wide limits, for example between 0.0005 and 10.0 kg/ha or more of active substance, but is preferably between 0.001 and 5 kg/ha.

The active substances according to the invention may be present in their commercially customary formulations, and in the application forms prepared from these formulations, as mixtures with other active substances, such as insecticides, attractants, sterilants, acaricides, nematicides, fungicides, growth regulators or herbicides. Examples of mixing partners include those described in The Pesticide Manual, edited by C D S Tomlin, 11th edition (1997), published by the British Crop Protection Council.

The active substance content of the use forms prepared from the commercially customary formulations can be from 0.00000001 to 95% by weight of active substance, preferably between 0.00001 and 1% by weight.

Application is effected in a conventional fashion, matched to the use forms.

The active substances according to the invention are also suitable for controlling ecto- and endoparasites in the veterinary medicine sector or in the sector of animal husbandry.

The active substances according to the invention are in this case applied in a known fashion, such as by oral application in the form of, for example, tablets, capsules, potions or granules, by dermal application in the form of, for example, dipping, spraying, pouring-on and spotting-on and powdering, and also by parenteral application in the form of, for example, injection.

The compounds, according to the invention, of the formula I can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since they are excreted in active form in the droppings, the development of insects in the animal droppings can be prevented very simply in this fashion. The dosages and formulations suitable in each case are particularly dependent on the type and stage of development of the productive animals and also on the degree of infestation, and can easily be determined and fixed by conventional methods. In the case of cattle, the novel compounds can be employed, for example, in dosages of 0.01 to 1 mg/kg of body weight.

Some compounds of the formula I according to the invention are also distinguished by a fungicidal action. Fungal pathogens which have already penetrated the plant tissue can be successfully subjected to curative control. This is particularly important and advantageous in the case of those fungal diseases which can no longer be controlled effectively with the otherwise customary fungicides when infection has taken place already. The spectrum of action of the claimed compounds embraces various economically important phytopathogenic fungi, for example *Plasmopara viticola, Phytophthora infestans, Erysiphe graminis, Pyricularia oryzae, Pyrenophora teres, Leptosphaeria nodorum, Pellicularia sasakii* and *Puccinia recondita*.

In addition, the compounds according to the invention are also suitable for use in technical fields, for example as wood preservatives, as preservatives in paints, in cooling lubricants for metalworking, or as preservatives in drilling and cutting oils.

In addition, the compounds of the invention can be applied to plants, or parts thereof, which have been genetically modified to exhibit a trait such as insect, fungal, bacterial viral and/or herbicidal resistance, and especially those plants containing a gene which expresses a *Bacillus thuringiensis* insecticide toxin. Transgenic plants with other traits may also be treated such as those which have been modified to alter the output of the plant, e.g. to increase the starch content of potatoes, or to modify the fatty acid spectrum in the oils of oil producing plants.

The invention also includes the use of any compound which will metabolise to the compounds of formula I either at the locus of the pest or in the pest itself.

The active substance content of the use forms prepared from commercially customary formulations can vary within wide limits, and the concentration of active substance in the use forms can be from 0.0001 up to 95% by weight of active substance, preferably between 0.0001 and 1% by weight. The formulations are applied in a customary manner adapted to suit the use forms.

The active compound content of the use forms prepared from the commercially customary formulations can vary within wide limits, and the concentration of active compound in the use forms can be from 0.0001 up to 95% by weight of active compound, preferably between 0.0001 and 1% by weight. The formulations are applied in a customary manner adapted to suit the use forms.

The examples which follow illustrate the invention without limiting it thereto.

A. FORMULATION EXAMPLES a) A dusting agent is obtained by mixing 10 parts by weight of active compound and 90 parts by weight of talc as inert material and comminuting in a hammer mill.

b) A wettable powder which is easily dispersible in water is obtained by mixing 25 parts by weight of active compound, 65 parts by weight of kaolin-containing quartz as inert material, 10 parts by weight of potassium ligninsulfonate and 1 part by weight of sodium oleoylmethyltaurate as wetting and dispersing agent, and grinding in a pinned disk mill.

c) A dispersion concentrate which is easily dispersible in water is prepared by mixing 40 parts by weight of active compound with 7 parts by weight of a sulfosuccinic monester, 2 parts by weight of a sodium ligninsulfonate and 51 parts by weight of water and grinding in a ball mill to a fineness of below 5 microns.

d) An emulsifiable concentrate can be prepared from 15 parts by weight of active compound, 75 parts by weight of cyclohexane as solvent and 10 parts by weight of ethoxylated nonylphenol (10 EO) as emulsifier.

e) Granules can be prepared from 2 to 15 parts by weight of active compound and an inert granule carrier material such as attapulgite, granulated pumice and/or quartz sand. It is expedient to use a suspension of the wettable powder of Example b) with a solids content of 30% which is sprayed onto the surface of attapulgite granules which are then dried and intimately mixed. The proportion by weight of the wettable powder in this case is about 5% and that of the inert carrier material is about 95% of the finished granules.

The examples which follow illustrate the invention without limiting it thereto.

Preparation Examples

Example A

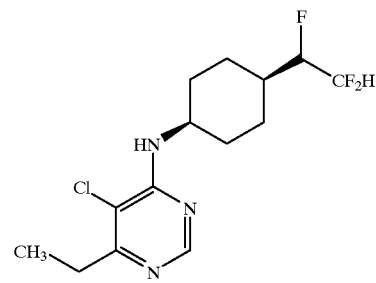

5-Chloro-4-cis[4-(1,2,2-trifluoroethyl)cyclohexylamino]-6-ethylpyrimidine

At 80° C., 0.8 g of 4-(1,2,2-trifluoroethyl)cyclohexylamine, 0.71 g of 4,5-dichloro-6-ethylpyrimidine and 1.1 g of potassium carbonate were stirred in 7 ml of DMF for 4 hours. The mixture was cooled to room temperature, mixed with water and extracted with ethyl acetate. The combined organic phases were washed with water, dried and concentrated. For purification and separation of the isomers, the crude product was chromatographed over silica gel (petroleum ether/ethyl acetate 7:3), to give the title product as a colourless oil. $^{19}$F NMR (CDCl$_3$) ppm: δ=−210.2 (1F, dm, J=405 Hz), −134.5, −131.5 (2F, AB-system, $J_{AB}$=297.5 Hz).

Example B

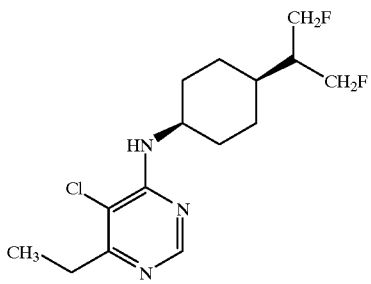

5-Chloro-6-ethyl-4-[cis-4-(2-fluoro-1-fluoromethylethyl)cyclohexylamino]pyrimidine At −70° C., a solution of 1.34 g of 2-{4-[(5-chloro-6-ethyl-4-pyrimidinyl)amino]cyclohexyl-1,3-propanediol in 25 ml of dichloromethane was mixed with 1.38 g of diethylaminosulfur trifluoride (DAST). The mixture was allowed to warm slowly to room temperature, stirring was continued for another 4 hours and the mixture was then stirred with aqueous sodium hydrogen bicarbonate. The organic phase was dried and concentrated. Silica gel chromatogaphy (ethyl acetate/methanol 19:1) gave the tiltle product as a colourless oil.

$^{19}$F NMR (CDCl$_3$) δ=−231.5 (dtr)

Example C

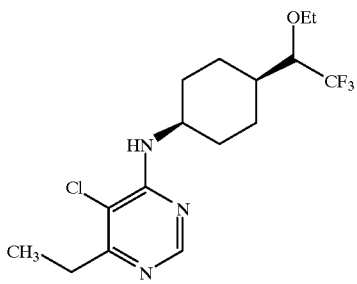

5-Chloro-6-ethyl-4-[cis-4-(1-ethoxy-2,2,2-trifluoroethyl)cyclohexylamino]pyrimidine 0.61 g of 5-chloro-6-ethyl-4-[cis-4-(1-hydroxy-2,2,2-trifluoroethyl)cyclohexylamino]pyrimidine were added to a suspension of 0.08 g of sodium hydride (80% dispersion in oil) in 10 ml of tetrahydrofuran, and the mixture was stirred at 50° C. until the evolution of hydrogen had ended. 0.28 g of diethyl sulfate were added, and the mixture was heated under reflux for 4 hours. The mixture was cooled to room temperature and a small amount of methanol was added dropwise to destroy excess sodium hydride, the mixture was concentrated and the residue was taken up in dilute ammonia solution and dichloromethane. The organic phase was dried and concentrated. Purification was carried out by silica gel chromatography (petroleum ether/ethyl acetate 1:1). to give the title product as a colourless oil.

$^{19}$F NMR (CDCl$_3$): −74.19 (d)

Example D

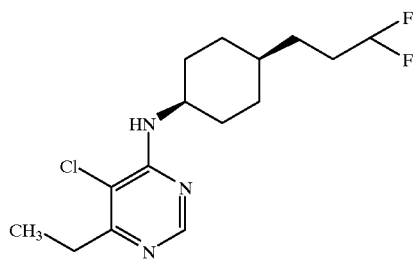

5-Chloro-6-ethyl-4-[cis-4-(3,3-difluoropropyl)cyclohexylamino]pyrimidine.

A solution of 7.0 g cis-3-(5-chloro-6-ethylpyrimidine-4-ylamino)propionaldehyde in 5 ml of chloroform was added slowly at 25° C. to a solution of 1.6 g diethylamino sulfur difluoride in 20 ml of chloroform. The mixture was stirred for 4 hours at room temperature and mixed with 100 ml of water. The organic layer was separated, washed in aqueous hydrogen with sodium carbonate and water, dried and concentrated. Chromatography of the crude product on silica gel (petroleum ether/ethyl acetate 4:1) gave the title product as a colourless oil.

$^1$F-NMR (CDCl$_3$): δ=−116 ppm.

Example E

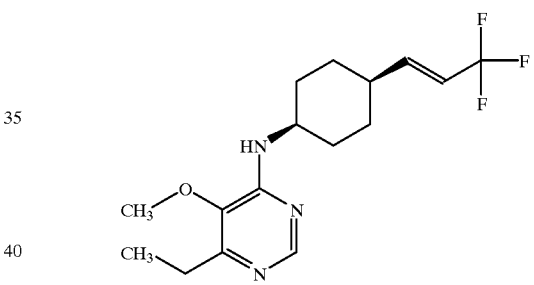

4-cis-[4-(3,3,3-E-trifluoropropenyl)cyclohexylamino]-6-ethyl-5-methoxypyrimidine At 130° C., 0.4 g of 4-cis-[4-(3,3,3-trifluoro-2-trifluoromethylsulfonyloxypropyl)cyclohexylamino]-6-ethyl-5-methoxypyrimidine was stirred with 0.5 ml of 1,8-diazabicyclo[5.4.0]undec-7-ene in 10 ml of xylene for 4 hours. The mixture was cooled to room temperature, washed with aqueous sodium hydrogen carbonate, the solvent removed and the residue chromatographed over silica gel (heptane/ethyl acetate), to give the title product as a colourless oil Preparation of Starting Materials Below are described methods of preparing starting materials of the products of Examples A to E and also to some of the compounds shown in the Tables below. Other starting materials are known or can be prepared in similar manner to one of the methods below or in known manner.

Example SM 1 a) 8-(2-chloro-1,2,2-trifluoroethylidene)-1,4-dioxaspiro[4.5]decane

At −100° C., 17.2 g of chlorotrifluoroethylene were condensed into 120 ml of tetrahydrofuran and 80 ml of diethyl ether. Over a period of 30 minutes, 84 ml of a 16 molar solution of n-BuLi in hexane were added dropwise at a temperature between −90° C. and −100° C. 18.8 g of 1,4-dioxaspiro[4.5]decane were added and the mixture was stirred at −60° C. for 1 h. The reaction solution was poured into aqueous ammonium chloride and extracted with diethyl ether and the combined organic phases were dried over magnesium sulfate and concentrated. The residue was taken up in 200 ml of pyrimidine and, at −30° C., mixed with 71 g of thionyl chloride. The reaction solution was slowly warmed to 0° C. and stirred for another 1.5 hours at this temperature. The reaction solution was poured onto ice and extracted with methylene chloride and the organic phase was dried over magnesium sulfate and concentrated. The residue was chromatographed over silica gel (petroleum ether:ethyl acetate 4:1), to give the title product as a yellow oil.

b) 8-(1,2,2-trifluoroethyl)-1,4-dioxaspiro[4.5]decane

At atmospheric pressure, 22 g of 8-(1,2,2-trifluoroethylidene)-1,4-dioxaspiro[4.5]decane in 250 ml of ethanol in the presence of palladium on carbon as catalyst were hydrogenated until 2.2 liter of hydrogen had been taken up. The catalyst was subsequently filtered off and the filtrate was concentrated. The residue was chromatographed over silica gel (petroleum ether/ethyl acetate, 7:1), to give the title product as a colourless oil.

c) 4-(1,2,2-trifluoroethyl)cyclohexanone

At 20 to 25° C., 6.2 g of 8-(1,2,2-trifluoroethyl)-1,4-dioxaspiro[4.5]decane were stirred in 40 ml of formic acid for 16 h. The reaction solution was subsequently poured into water, adjusted to pH 8 using potassium carbonate, extracted with methylene chloride and the organic phase was dried and concentrated to give the title product as a colourless oil which was reacted further without any purification.

d) 4-(1,2,2-trifluoroethyl)cyclohexylamine (starting material for Example A)

At 50° C. and 20 bar hydrogen pressure, 4.7 g of 4-(1,2,2-trifluoroethyl)cyclohexanone were reductively aminated in 100 ml of ammonia-saturated methanol in an autoclave using rhodium on carbon as catalyst. The catalyst was filtered off and the reaction solution was concentrated, giving the title product as a brown oil which was reacted further without any purification.

Example SM 2 a) 8-(2,2,2-trifluoroethylidene)-1,4-dioxaspiro[4.5]decane

At −100° C., 22 g of 1,1-difluoroethylene were condensed into a solvent mixture of 400 ml of tetrahydrofuran and 100 ml of diethyl ether. Subsequently, 153 ml of a 1.3 molar solution of sec-BuLi were added dropwise to the reaction solution at a temperature between −90° C. and −100° C. Finally, 31.2 g of 1,4-dioxaspiro[4.5]decane were added, the solution was stirred at −100° C. for another 20 minutes and subsequently warmed to 0° C. with stirring. The reaction solution was poured into an aqueous ammonium chloride and extracted with methylene chloride and the combined organic phases were dried over magnesium sulfate and concentrated. The residue was taken up in 400 ml of methylene chloride and, at −70° C., reacted with 32 g (0.2 mol) of DAST, dissolved in 100 ml of methylene chloride. The mixture was then slowly warmed to 0° C. with stirring, and the reaction solution was subsequently poured into an aqueous ammonium chloride. The product was extracted with diethyl ether and the combined organic phases were dried over $MgSO_4$ and concentrated. The residue was chromatographed over silica gel (petroleum ether/ethyl acetate 4:1), to give the title product as a colourless oil.

b) 4-(2,2,2-trifluoroethyl)cyclohexanone

At atmospheric pressure, 22.0 g of 8-(2,2,2-trifluoroethylidene)-1,4-dioxaspiro[4.5]decane in 250 ml of ethanol were hydrogenated in the presence of palladium on carbon as catalyst until no further uptake of hydrogen was visible. The catalyst was subsequently filtered off and the filtrate was concentrated. The residue was taken up in 170 ml of formic acid and stirred at 20° C. to 25° C. for 4 h. The reaction solution was poured into water, adjusted to pH 8 with potassium carbonate and extracted with methylene chloride. The combined organic phases were dried with magnesium sulfate and concentrated to give the title product as a colourless oil which was reacted further without any purification.

c) 4-(2,2,2-trifluoroethyl)cyclohexylamine

This was obtained in a similar manner to Example SM1(e) as a brown oil which was reacted further without any purification.

Example SM 3

In a similar manner to Example SM2, 1,4-dioxaspiro[4.5] decane was reacted with 1,1,3,3,3-pentafluoropropene to give 8-(2,2,2-trifluoro-1-trifluoromethylethylidene)-1,4-dioxaspiro[4.5]decane, as a colourless oil, which in turn was converted to 4-(2,2,2-trifluoro-1-trifluoromethylethyl) cyclohexanone and 4-(2,2,2-trifluoro-1-trifluoromethylethyl)cyclohexylamine as a brown oil.

Example SM 4 a) 1-benzyloxy-4-(3,3,3-trifluoro-1-propenyl)benzene

At 130° C., 96 g of 3,3,3-trifluoropropene, 155 g of 1-benzyloxy-4-iodobenzene, 68.5 g of potassium acetate and 0.85 g of $PdCl_2$ in 750 ml of methanol were reacted in an autoclave for 20 hours. After cooling to room temperature, the reaction mixture was mixed with water and extracted with ether. The combined organic phases were washed with water, dried and concentrated to give the title product as a colourless crystalline powder, which was reacted further without any purification.

b) 4-(3,3,3-trifluoropropyl)phenol 30 g (0.11 mol) of 1-benzyloxy-4-(3,3,3-trifluoropropene-1-propenyl)benzene were hydrogenated in 400 ml of glacial acetic acid at 50° C. and 20 bar hydrogen pressure using palladium on carbon as catalyst for 12 h. The catalyst was filtered off and the reaction solution was concentrated, to give the title product as a colourless solid which was reacted further without any purification.

c) 4-(3,3,3-trifluoropropyl)cyclohexanol

At 50° C. and 150 bar hydrogen pressure, 40.7 g of 4-(3,3,3-trifluoropropyl)phenol in 800 ml of isopropanol were hydrogenated using rhodium on carbon as catalyst for 20 h. The catalyst was filtered off and the reaction solution was concentrated, to give the title product as a colourless solid which was reacted further without any purification.

d) 4-(3,3,3-Trifluoropropyl)cyclohexanone 35.6 g of 4-(3,3,3-trifluoropropyl)cyclohexanol were dissolved in 600 ml of acetone and 37 ml of water and mixed with 69 ml of Jones reagent. The mixture was stirred at room temperature for 24 h, mixed with 9 ml of isopropanol and 24 g of sodium hydrogen carbonate, the precipitate was filtered off and the residue was taken up in saturated aqueous sodium chloride. The mixture was extracted with ether and the combined ether phases were washed with water, dried and concentrated. Chromatography over silica gel (petroleum ether/ethyl acetate=3:1) gave the title product as a colourless oil.

e) 4-(3,3,3-Trifluoropropyl)cyclohexylamine

This was obtained in a similar manner to Example SM1 (d) as a brown oil which was reacted further without any purification.

Example SM 5 a) 1-(2,2-difluoro-1-methylvinyl)-4-methoxybenzene

At between 0° C. and −10° C., 181 g of tris (dimethylamino)phosphine in 75 ml of triglyme were added dropwise to 84 g of dibromodifluoromethane in 50 ml of triglyme. At 0° C., 30 g of 4-methoxyacetophenone dissolved in 125 ml of triglyme were subsequently added dropwise and the mixture was stirred for ½ h at room temperature and for 24 h at 80° C. The mixture was cooled to room temperature, mixed with 200 ml of water and extracted with petroleum ether. The combined organic phases were dried and concentrated. For purification, the crude product was chromatographed over silica gel (petroleum ether/ethyl acetate 5:1), to give the title product as a colourless oil.

b) 1-(2,2-difluoro-1-methylethyl)-4-methoxybenzene

At 50° C. and 1 atm hydrogen pressure, 24.2 g of 1-(2,2-difluoro-1-methylvinyl)-4-methoxybenzene in 300 ml of glacial acetic acid were hydrogenated using palladium on carbon as catalyst until no further hydrogen uptake was visible. The catalyst was filtered off and the reaction solution was concentrated, to give the title product as a colourless oil which was reacted further without any purification.

c) 4-(2,2-difluoro-1-methylethyl)phenol 24.8 g (0.13 mol) of 1-(2,2-difluoro-1-methylethyl)-4-methoxybenzene were stirred in 350 ml of glacial acetic acid and heated under reflux. 67 g of 48% aqueous hydrobromic acid were subsequently added dropwise and the mixture was stirred under reflux for a further 5 h. After cooling to room temperature, the solvent was distilled off under reduced pressure and the residue was taken up in ethyl acetate, washed with aqueous sodium hydrogen carbonate dried and concentrated to give the title product as a colourless oil which was reacted further without any purification.

d) 4-(2,2-difluoro-1-methylethyl)cyclohexanol

At 50° C. and 150 bar, 19.7 g of 4-(2,2-difluoro-1-methylethyl)phenol in 150 ml of isopropanol were hydrogenated in the presence of rhodium on carbon as catalyst for 20 h. The catalyst was filtered off and the reaction solution was concentrated, giving 16.9 g (83% of theory) of product as a colourless oil which was reacted further without any purification.

e) 4-(2,2-difluoro-1-methylethyl)cyclohexanone

This was obtained in a similar manner to Example SM4(e) as a colourless oil which was reacted further without any purification.

f) 4-(2,2-difluoro-1-methylethylcyclohexylamine

This was obtained in a similar manner to Example SM1 (d) as a brown oil which was reacted further without any purification.

Example SM 6 a) 4-perfluoroethyl-1-nitrobenzene

In a bomb, 2.0 g of 4-iodo-1-nitrobenzene together, 6.5 g of perfluoroethyl iodide and 0.6 g (9.3 mmol) of copper in 50 ml of DMSO were heated at 130° C. for 28 h. The mixture was filtered, the filtrate concentrated under reduced pressure, and the crude product was chromatographed over silica gel (petroleum ether/ethyl acetate 1:1), to give the title product.

b) 4-perfluoroethylaniline 9.4 g of 4-perfluoroethyl-1-nitrobenzene were dissolved in 60 ml of ethanol and 30 ml of glacial acetic acid and 5.7 g iron powder added portionwise with stirring. The mixture was stirred under reflux for 4 h, cooled, filtered and the filtrate concentrated under reduced pressure. The residue was mixed with water and extracted with ethyl acetate. The extract was with water, dried and concentrated. The crude product was chromatographed over silica gel (petroleum ether/ethyl acetate=1:1), to give the title product as a colourless oil.

c) 4-perfluoroethylcyclohexylamine

At 50° C. and 70 bar hydrogen pressure, 5.2 g of 4-perfluoroethylaniline in 60 ml of absolute ethanol were hydrogenated for 10 h using ruthenium oxide as catalyst. The catalyst was filtered off and the filtrate was concentrated to give the title product as a colourless oil which was reacted further without any purification.

Example SM 7 a) 4'-methoxy-2,2,2-trifluoroacetophenone

At −60° C., a solution of 10.5 g of 4-methoxyphenylmagnesium bromide in 50 ml of THF was added dropwise over a period of 1 hour to a solution of 7.2 g of methyl trifluoroacetate in 50 ml of ether. Stirring was then continued at −20° C. for 2 hours and at 0° C. for a further hour. The reaction solution was mixed with 25 ml of 2N hydrochloric acid and extracted with ethyl acetate. The extract was dried and concentrated. The residue was distilled under reduced pressure (b.p. 41° C., $4.5 \times 10^{-1}$ torr), to give the title product as a colourless oil.

b) 1,1,1-trifluoro-2-(4-methoxyphenyl)-2-propanol

At −15° C., 18 ml of a 3 M solution of methylmagnesium chloride in ether were added dropwise to a solution of 5.8 g of 4'-methoxy-2,2,2-trifluoroacetophenone in 35 ml of ether, and the mixture was stirred at room temperature for 5 h. The reaction solution was hydrolysed with aqueous ammonium chloride and extracted with ether. The extract was dried and to give the title product as a colourless oil, which was reacted further without any purification.

c) 4-[1-(trifluoromethyl)vinyl]-1-methoxybenzene 9.0 g of 1,1,1-trifluoro-2-(4-methoxyphenyl)-2-propanol were heated with 0.4 g of p-toluenesulfonic acid hydrate in 30 ml of glacial acetic acid until the elimination of water had ended. The reaction solution was concentrated, the residue was taken up in water, neutralised with aqueous sodium hydrogen carbonate and extracted with ethyl acetate. The extract was washed with water, dried and concentrated. Distillation of the residue under reduced pressure ($5.1 \times 10^{-1}$ torr) gave the title product as a colourless oil.

d) 4-(2,2,2-trifluoro-1-methylethyl)phenol

At 60 to 70° C. and under atmospheric pressure, 9.2 g of 4-[1-(trifluoromethyl)vinyl]-1-methoxybenzene in 50 ml of glacial acetic acid were hydrogenated in the presence of 0.26 g of Pd/C (10%) until no further uptake was visible. The catalyst was filtered off, the reaction solution was mixed with 22.7 g of aqueous hydrobromic acid (48%) and heated under reflux for 21 h. The reaction solution was concentrated, taken up in ethyl acetate, washed with aqueous sodium hydrogen carbonate, dried and concentrated to give the title product which was reacted further without any purification.

e) 4-(2,2,2-trifluoro-1-methylethyl)cyclohexanol

This was obtained in a similar manner to Example SM4 (d) as an oil which was reacted further without any purification f) 4-(2,2,2-trifluoro-1-methylethyl)cyclohexanone This was obtained in a similar manner to Example SM4(e) as an oil which was reacted further without any purification g) 4-(2,2,2-trifluoro-1-methylethyl)cyclohexylamine This was obtained in a similar manner to Example SM1 (d) as a brown oil which was reacted further without any purification.

Example SM 8 a) dimethyl (4-hydroxyphenyl)malonate

At room temperature and a hydrogen pressure of 5 bar, 94.3 g of diethyl (4-benzyloxyphenyl)malonate (J. Org. Chem. 46, 3007 (1981)) in 500 ml of methanol were hydrogenated in the presence of 5 g of palladium/carbon catalyst (5%). The catalyst was filtered off and the mixture was concentrated, to give the title product as a colourless oil.

b) dimethyl (4-hydroxycyclohexyl)malonate

At 60° C. and a hydrogen pressure of 150 bar, 67.3 g of dimethyl (4-hydroxyphenyl)malonate in 500 ml of methanol were hydrogenated in the presence of 5 g of rhodium/carbon catalyst (5%). The catalyst was filtered off and the mixture was concentrated. This to give the title product as a colourless oil.

c) dimethyl (4-oxocyclohexyl)malonate

At 5° C., a mixture of 22.7 g of sodium dichromate dihydrate, 17 ml of concentrated sulfuric acid and 113 ml of water was added dropwise to a solution of 47.7 g of dimethyl (4-hydroxycyclohexyl)malonate in 250 ml of diethyl ether. The mixture was stirred at room temperature for 4 hours, the organic phase was separated off and the aqueous phase was once more extracted with diethyl ether. The combined organic phases were dried and concentrated to give the title product as a yellow oil which was used without any further purification for the next step.

d) dimethyl (cis-4-benzylaminocyclohexyl)malonate 34.0 g of dimethyl (4-oxocyclohexyl)malonate and 16.1 g of benzylamine in 200 ml of methanol were reacted at 65° C. and 5 bar hydrogen pressure in the presence of 5 g of palladium/carbon catalyst (5%). The catalyst was filtered off and the mixture was concentrated. The cis/trans isomers were separated by silica gel chromatography (ethyl acetate/methanol 19:1).

The desired cis isomer eluted before the trans isomer e) dimethyl (cis-4-aminocyclohexyl)malonate 23.0 g of dimethyl (cis-4-benzylaminocyclohexyl) malonate were dissolved in 200 ml of methanol and hydrogenated at 30 bar and 50° C. in the presence of 2 g of palladium catalyst (5% on carbon). Removal of the catalyst by filtration and subsequent concentration gave 16.0 g of the title product as a colourless oil.

f) dimethyl [cis-4-(4-chloro-6-ethylpyrimidin-4-ylamino) cyclohexyl]malonate 11.6 g (65 mmol) of 4,5-dichloro-6-ethylpyridimine, 15.0 g (65 mmol) of dimethyl (cis-4-aminocyclohexyl)malonate and 18 ml (130 mmol) of triethylamine in 100 ml of toluene were heated under reflux for 8 hours. The mixture was stirred with water, and the organic phase was dried and concentrated. For purification, the crude product was subjected to silica gel chromatography (ethyl acetate), to give the title product as a colourless oil which slowly solidified, m.p. 82 to 83° C.

g) 2-{4-[(5-chloro-6-ethyl-4-pyrimidinyl)amino] cyclohexyl-1,3-propanediol

A solution of 9.9 g of dimethyl [cis-4-(4-chloro-6-ethylpyrimidine-4-ylamino)cyclohexyl]malonate in 20 ml of dry ether was added dropwise to a suspension of 2.0 g of lithium aluminium hydride in 150 ml of dry ether. The mixture was stirred at room temperature for 2 hours and subsequently heated under reflux for 2 hours. The mixture was cooled to room temperature and carefully decomposed by dropwise addition of water, inorganic material was filtered off and the filtrate was dried and concentrated. A colourless resin remained, which was subjected to silica gel chromatography (ethyl acetate/methanol 9:1) for purification to give the title product as a colourless oil.

Example SM 9 a) 4'-benzyloxy-2,2,2-trifluoroacetophenone

At –78° C., 182.4 ml of a 2.5 M butyllithium solution were added dropwise to a solution of 100 g of 4-benzyloxy-1-bromobenzene in 500 ml of dry tetrahydrofuran. Stirring was continued at –78° C. for 15 min, and 68.0 g of methyl trifluoroacetate were then added dropwise at this temperature. Stirring was subsequently continued at –20° C. for 2 hours. For work-up, 80 ml of saturated aqueous ammonium chloride were added dropwise, the mixture was mixed with 250 ml of dilute hydrochloric acid and diluted with 500 ml of toluene, and the organic phase was washed with water, dried and concentrated, to give the title product as a colourless oil which crystallised on digestion with heptane.

b) 1-benzyloxy-4-(1-hydroxy-2,2,2-trifluoroethyl) benzene

At 20° C., a solution of 15.7 g of sodium borohydride in 100 ml of water was added dropwise with cooling to a solution of 72.5 g of 4'-benzyloxy-2,2,2-trifluoroacetophenone in 900 ml of ethanol. The mixture was stirred under reflux for 3 hours and then concentrated, the residue was taken up in diethyl ether and water and made slightly acidic using dilute hydrochloric acid, and the organic phase was dried and concentrated to give the title product as a colourless oil.

c) 4-(1-hydroxy-2,2,2-trifluoroethyl)phenol

At 50° C. and a hydrogen pressure of 5 bar, 65.7 g (233 mmol) of 1-benzyloxy-4-(1-hydroxy-2,2,2-trifluoroethyl) benzene were hydrogenated in the presence of 5.2 g of palladium (10% on carbon) in 500 ml of glacial acetic acid. The catalyst was filtered off and the mixture was concentrated. This gave 44.1 g (99% of theory) of the product as a colourless oil.

d) 4-(1-hydroxy-2,2,2-trifluoroethyl)cyclohexanol

At 50° C. and a hydrogen pressure of 150 bar, 44.1 g of 4-(1-hydroxy-2,2,2-trifluoroethyl)phenol were hydrogenated in the presence of 3 g of rhodium (5% on carbon) in 500 ml of isopropanol. The catalyst was filtered off and the mixture was concentrated, to give the title product as a colourless oil.

e) 4-(1-hydroxy-2,2,2-trifluoroethyl)cyclohexanone

At room temperature, 56.2 g (284 mmol) of 4-(1-hydroxy-2,2,2-trifluoroethyl)cyclohexanol and 91.7 g of pyridinium chlorochromate were stirred in 1 l of dichloromethane for 8 hours. The solvent was removed under reduced pressure and the residue was purified by filtration through silica gel (heptane/ethyl acetate 1:1), to give the title product as a colourless oil.

f) cis-1-benzylamino-4-(1-hydroxy-2,2,2-trifluoroethyl) cyclohexane

At 50° C. and a hydrogen pressure of 5 bar, 43.0 g of 4-(1-hydroxy-2,2,2-trifluoroethyl)cyclohexanone and 24.0 g of benzylamine in 400 ml of methanol were hydrogenated in the presence of 1.5 g of platinum (5% on carbon). The catalyst was filtered off and the mixture was concentrated. The cis/trans isomers were separated by silica gel chromatography (ethyl acetate/ethanol 9:1). The cis isomer eluted first of the two isomers, to give the title product as a colourless oil.

g) cis-4-(1-hydroxy-2,2,2-trifluoroethyl)cyclohexylamine

At 50° C. and a hydrogen pressure of 30 bar, 33.6 g of cis-1-benzylamino-4-(1-hydroxy-2,2,2-trifluoroethyl) cyclohexane were hydrogenated in the presence of 2 g of palladium (10% on carbon) in 250 ml of methanol. The catalyst was filtered off and the mixture was concentrated to give the title product as a colourless oil.

h) 5-chloro-6-ethyl-4-[cis-4-(1-hydroxy-2,2,2-trifluoroethyl)cyclohexylamino]pyrimidine 1.3 g of 4,5-dichloro-6-ethylpyrimidine, 2.0 g of cis-4-(1-hydroxy-2,2,2-trifluoroethyl)cyclohexylamine and 1.5 g of potassium carbonate in 20 ml of dimethylformamide were stirred at 90° C. for 3 hours. For work-up, the mixture was concentrated, the residue was taken up in dichloromethane and water and the organic phase was dried and concentrated. Purification was carried out by silica gel chromatography (petroleum ether/ethyl acetate 1:1) to give the title product as a colourless solid.

Example SM 10 a) 1-(4-benzyloxyphenyl)-1,1,1-trifluoro-2-propanol

At 0° C., 50 ml of a 3.0 M solution of methylmagnesium chloride were added dropwise to a solution of 32 g of 4'-benzyloxy-2,2,2-trifluoroacetophenone (product of SM9a) in 150 ml of diethyl ether. The mixture was subsequently heated under reflux for 3 hours. For work-up, the mixture was poured on aqueous saturated ammonium chloride and the organic phase was dried and concentrated, to give the title product. as a colourless oil.

b) 1-benzyloxy-4-(1-methoxy-1-methyl-2,2,2-trifluoroethyl)benzene 32.3 g of 1-(4-benzyloxyphenyl)-1,1,1-trifluoro-2-propanol, 19.7 g of dimethyl sulfate and 13.7 g of potassium carbonate in 100 ml of acetone were heated under reflux for 3 days. For work-up, the mixture was concentrated, the residue was taken up in dichloromethane/ammonia solution and the organic phase was dried and concentrated. The crude product was chromatographed on silica gel (petroleum ether/ethyl acetate 3:1), to give the title product, as a colourless oil.

c) 4-(1-methoxy-1-methyl-2,2,2-trifluoroethyl)phenol

At 50° C. and a hydrogen pressure of 5 bar, 24.5 g of 1-benzyloxy-4-(1-methoxy-1-methyl-2,2,2-trifluoroethyl) benzene in 150 ml of glacial acetic acid were hydrogenated in the presence of 1.4 g of palladium (10% on carbon). The catalyst was filtered off and the mixture was concentrated to give the title product as a colourless oil.

d) 4-(1-methoxy-1-methyl-2,2,2-trifluoroethyl) cyclohexanol

This was obtained in a similar manner to Example SM4 (d) as a colourless oil.

e) 4-(1-methoxy-1-methyl-2,2,2-trifluoroethyl) cyclohexanone

This was obtained in a similar manner to Example SM4 (e), as a colourless oil f) cis-1-benzylamino-4-(1-methoxy-1-methyl-2,2,2-trifluoroethyl)cyclohexane In a similar to Example SM9(f), the title product was obtained as a colourless oil.

g) cis-4-(1-methoxy-1-methyl-2,2,2-trifluoroethyl) cyclohexylamine

This was obtained in a similar manner to Example SM4 (g), as a colourless oil

Example SM 11 cis-3-(5-chloro-6-ethylpyrimidine-4-ylamino) propionaldehyde

To a mixture of 2.8 g cis-3-(5-chloro-6-ethylpyrimidine-4-ylamino)propanol, 15.15 g triethylamine and 35 ml dimethyl sulfoxide in 50 ml of toluene, was added portionwise, 23.8 g of sulfur trioxide-pyridine complex at 5° C. The mixture was stirred for 2 hours at 30° C. With cooling, the mixture was hydrolysed by the addition of water and extracted with toluene. The extract was dried and concentrated. The residue was chromatographed on silica gel (heptane/ethyl acetate 2:3), to give the title product, as a colourless oil.

Example SM 12 a) 4-(3,3,3-trifluoro-2-hydroxypyropyl)nitrobenzene

At 0° C., 152 ml of $BF_3$-THF complex (1M) was added dropwise to 30 g of 4-(3,3,3-trifluoropropenyl)nitrobenzene (Synthesis 1981, 365) in 150 ml of THF. The mixture was heated under reflux for 6 hours, cooled to 0° C. and 36 ml hydrogen peroxide added dropwise. The mixture was allowed to stand overnight, acidified to pH 3 with 2N hydrochloric acid and extracted with ether. The solvent was removed and the residue was chromatographed on silica gel (heptane/ethyl acetat3), to give the title product, as a colourless.

b) cis/trans-4-(3,3,3-trifluoro-2-hydroxypropyl) cyclohexylamine 28 ml of 4-(3,3,3-trifluoro-2-hydroxypropyl)nitrobenzene was hydrogenated at a hydrogen pressure of 100 bar, in the presence of 2.8 g of rhodium/carbon catalyst (5%) and 1.4.g sulfuric acid in 100 ml methanol. The catalyst was filtered off and the mixture was concentrated. This to give the title product as a colourless oil.

c) 4-[cis-4-(3,3,3-trifluoro-2-hydroxypropyl) cyclohexylamino]-6-ethyl-5-methoxypyrimidine 25 g cis/trans-4-(3,3,3-trifluoro-2-hydroxypropyl) cyclohexylamine and 76 g of 5-bromo-4-chloro-6-ethylpyrimidine were heated with 19.8 g potassium carbonate in 40 ml water and 20 ml toluene at 110° C. for 5 hours. The mixture was extracted with ethyl acetate and the extract washed with aqueous sodium chloride and concentrated.

47.1 g of crude product was heated with 4.7 g copper(I) bromide in 200 ml sodium methoxide solution (30%) for 5 hours at 100° C. After cooling the mixture was poured into saturated aqueous ammonium chloride and extracted with dichloromethane. the solvent was evaporated and the residue purified by silica gel chromatography (heptane/ethyl acetate 1:1) to give the title product.

d) 4-cis-[4-(3,3,3-trifluoro-2-trifluoromethylsulfonyloxypropyl)cyclohexylamino]-6-ethyl-5-methoxypyrimidine 0.43 g of 4-[cis-4-(3,3,3-trifluoro-2-hydroxypropyl) cyclohexylamino]-6-ethyl-5-methoxypyrimidine was added to a stirred mixture of trifluoromethanesulfonic anhydride and 0.14 ml pyridine in 5 ml dichloromethane. The mixture was stirred for 5 hours at 40° C., washed with aqueous sodium hydrogen carbonate and dried. Solvent was removed to give the title product.

The following two examples illustrate the fluorination process

Example E

Fluorination with F-TEDA-BF$_4$ 4-(cis-4-tert-butylcyclohexylamino)-6-ethyl-5-fluoropyrimidine

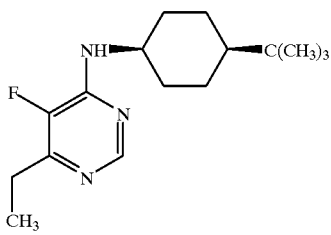

Preparation of 4-(cis-4-tert-butylcyclohexylamino)-6-ethylpyrimidine 14.3 g of 4-chloro-6-ethylpyrimidine and 17.1 g of cis-4-tert-butylcyclohexylamine were heated to 80 to 90° C. with 15.2 g of triethylamine in 75 ml of toluene for 8 hours. After cooling, the mixture was stirred with water and the organic phase was dried and concentrated. For purification, the mixture was chromatographed over silica gel (ethyl acetate). This gave the title product as a colourless oil.

Preparation of the end product

At room temperature, 3.0 of 4-(cis-4-tert-butylcyclohexylamino)-6-ethyl)pyrimidine and 5.3 g of F-TEDA-BF$_4$ in 300 ml of acetonitrile were stirred for 24 hours. For work-up, the mixture was diluted with diethyl ether and stirred with water and aqueous sodium bicarbonate solution. The organic phase was dried and concentrated and the residue was chromatographed over silica gel (petroleum ether/ethyl acetate 9:1). In addition to 0.45 g of product (colourless oil), 1.64 g of non-fluorinated starting material were recovered.

Yield: 31% of theory, based on recovered starting material $^1$H NMR (300 MHz, CDCl$_3$)

δ=8.40 (d, 1H), 5.60 (s, NH), 4.32 (m, 1H), 2.79 (dq, 2H); 1.85–2.02 (m, 2H); 1.50–1.75 (m, 4H); 1.00–1.15 (m, 3H); 1.29 (tr, 3H); 0.88 (s, 9H, 3CH$_3$)

Example G

Fluorination with elementary fluorine 4-(cis-4-tert-butylcyclohexylamino)-6-ethyl-5-fluoropyrimidine

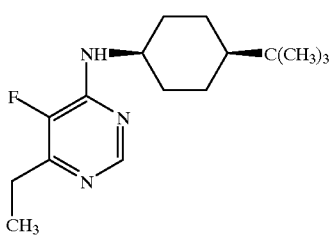

A solution of 2.62 g of 4-(cis-4-tert-butylcyclohexylamino)-6-ethyl pyrimidine in 40 ml of trifluoroacetic acid was charged into a reactor for direct fluorination. A stream of a mixture of F$_2$/N$_2$ (1:10 by volume) was passed through the mixture at 15° C. After 0.015 mol of fluorine was passed through, the reaction was flushed with nitrogen in order to remove unconsumed fluorine. The solvent was removed in vacuo and the residue was treated with 50 ml of 2N sodium hydroxide, extracted with diethyl ether, washed with water and dried over MgSO$_4$. After ether evaporation, the product was isolated in 41% yield by column chromatography, eluting with a mixture hexane/ethyl acetate 2:1.

NMR $^{19}$F (CDCl$_3$) d=–159.2 ppm.

The following table illustrates the compounds of the invention, which can be prepared by the methods of the previous Examples. The table includes the products of these Examples

TABLE 1

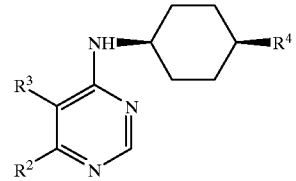

| Ex No | R$^2$ | R$^3$ | R$^4$ | Physical data |
|---|---|---|---|---|
| 1 | CH$_3$ | Cl | CF$_2$CF$_3$ | |
| 2 | CH$_3$ | Cl | CH$_2$CF$_3$ | |
| 3 | CH$_3$ | Cl | CH(F)CF$_2$H | |
| 4 | CH$_3$ | Cl | CH(F)CF$_3$ | |
| 5 | CH$_3$ | Cl | CH$_2$CF$_2$H | |
| 6 | CH$_3$ | Cl | CH(CH$_3$)CF$_3$ | oil |
| 7 | CH$_3$ | Cl | CH(CH$_3$)CF$_2$H | |
| 8 | CH$_3$ | Cl | CH(CF$_3$)CF$_3$ | |
| 9 | CH$_3$ | Cl | CF(CF$_3$)CF$_3$ | |
| 10 | CH$_3$ | Cl | CH(CF$_2$H)CF$_3$ | |
| 11 | CH$_3$ | Cl | CH(CF$_2$H)CF$_2$H | |
| 12 | CH$_3$ | Cl | CF(CH$_3$)CF$_3$ | |
| 13 | CH$_3$ | Cl | CF(CF$_2$H)CH$_3$ | |
| 14 | CH$_3$ | Cl | CH$_2$CH$_2$CF$_3$ | oil |
| 15 | CH$_3$ | Cl | CF$_2$CF$_2$CF$_3$ | |
| 16 | CH$_3$ | Cl | CH$_2$CF$_2$CF$_3$ | |
| 17 | CH$_3$ | Cl | CH(F)CF$_2$CF$_3$ | |
| 18 | CH$_3$ | Cl | CF$_2$CF$_2$CF$_2$CF$_3$ | |
| 19 | CH$_3$ | Cl | CH$_2$CF$_2$CF$_2$CF$_3$ | |
| 20 | CH$_3$ | Cl | CH$_2$CH$_2$CF$_2$CF$_3$ | |
| 21 | CH$_3$ | Cl | CH$_2$CH$_2$CH$_2$CF$_3$ | |
| 22 | CH$_3$ | Cl | CH(CF$_3$)CH$_2$CH$_3$ | |
| 23 | CH$_3$ | Cl | CF(CF$_3$)CH$_2$CH$_3$ | |
| 24 | CH$_3$ | Cl | CF(CH$_3$)CH$_2$CH$_3$ | |
| 25 | CH$_3$ | Cl | CF(CH$_3$)CF$_2$CF$_3$ | |
| 26 | CH$_3$ | Cl | CH(CH$_3$)CF$_2$CF$_3$ | |
| 27 | CH$_3$ | Cl | CH$_2$CF(CF$_3$)2 | |
| 28 | CH$_3$ | Cl | CF(CF$_3$)CF$_2$CF$_3$ | |
| 29 | CH$_3$ | Cl | CH(CF$_3$)CF$_2$CF$_3$ | |
| 30 | CH$_3$ | Cl | CH(CF$_2$H)CH$_2$CH$_3$ | |
| 31 | CH$_3$ | Cl | CH(CF$_2$H)CF$_2$CF$_3$ | |
| 32 | CH$_2$OCH$_3$ | OCH$_3$ | CF$_2$CF$_3$ | |
| 33 | CH$_2$OCH$_3$ | OCH$_3$ | CH$_2$CF$_3$ | |
| 34 | CH$_2$OCH$_3$ | OCH$_3$ | CH(F)CF$_2$H | |
| 35 | CH$_2$OCH$_3$ | OCH$_3$ | CH(F)CF$_3$ | |
| 36 | CH$_2$OCH$_3$ | OCH$_3$ | CH$_2$CF$_2$H | |
| 37 | CH$_2$OCH$_3$ | OCH$_3$ | CH(CH$_3$)CF$_3$ | oil |
| 38 | CH$_2$OCH$_3$ | OCH$_3$ | CF(CF$_2$H)CH$_3$ | oil |
| 39 | CH$_2$OCH$_3$ | OCH$_3$ | CH(CH$_3$)CF$_2$H | oil |
| 40 | CH$_2$OCH$_3$ | OCH$_3$ | CH(CF$_3$)CF$_3$ | |
| 41 | CH$_2$OCH$_3$ | OCH$_3$ | CF(CF$_3$)CF$_3$ | |
| 42 | CH$_2$OCH$_3$ | OCH$_3$ | CH(CF$_2$H)CF$_3$ | |
| 43 | CH$_2$OCH$_3$ | OCH$_3$ | CH(CF$_2$H)CF$_2$H | |
| 44 | CH$_2$OCH$_3$ | OCH$_3$ | CF(CH$_3$)CF$_3$ | |
| 45 | CH$_2$OCH$_3$ | OCH$_3$ | CH$_2$CH$_2$CF$_3$ | oil |
| 46 | CH$_2$OCH$_3$ | OCH$_3$ | CF$_2$CF$_2$CF$_3$ | |
| 47 | CH$_2$OCH$_3$ | OCH$_3$ | CH$_2$CF$_2$CF$_3$ | |
| 48 | CH$_2$OCH$_3$ | OCH$_3$ | CH(F)CF$_2$CF$_3$ | |
| 49 | CH$_2$OCH$_3$ | OCH$_3$ | CF$_2$CF$_2$CF$_2$CF$_3$ | |

TABLE 1-continued

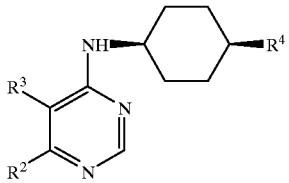

| Ex No | R² | R³ | R⁴ | Physical data |
|---|---|---|---|---|
| 50 | CH₂OCH₃ | OCH₃ | CH₂CF₂CF₂CF₃ | |
| 51 | CH₂OCH₃ | OCH₃ | CH₂CF₂CF₂CF₃ | |
| 52 | CH₂OCH₃ | OCH₃ | CH₂CH₂CH₂CF₃ | |
| 53 | CH₂OCH₃ | OCH₃ | CH(CF₃)CH₂CH₃ | oil |
| 54 | CH₂OCH₃ | OCH₃ | CF(CF₃)CH₂CH₃ | |
| 55 | CH₂OCH₃ | OCH₃ | CF(CF₃)CH₂CH₃ | |
| 56 | CH₂OCH₃ | OCH₃ | CF(CH₃)CF₂CF₃ | |
| 57 | CH₂OCH₃ | OCH₃ | CH(CH₃)CF₂CF₃ | |
| 58 | CH₂OCH₃ | OCH₃ | CH₂CF(CF₃)2 | |
| 59 | CH₂OCH₃ | OCH₃ | CF(CF₃)CF₂CF₃ | |
| 60 | CH₂OCH₃ | OCH₃ | CH(CF₃)CF₂CF₃ | |
| 61 | CH₂OCH₃ | OCH₃ | CH(CF₂H)CH₂CH₃ | |
| 62 | CH₂OCH₃ | OCH₃ | CH(CF₂H)CF₂CF₃ | |
| 63 | CH₂CH₃ | Br | CF₂CF₃ | |
| 64 | CH₂CH₃ | Br | CH₂CF₃ | |
| 65 | CH₂CH₃ | Br | CH(F)CF₂H | |
| 66 | CH₂CH₃ | Br | CH(F)CF₃ | |
| 67 | CH₂CH₃ | Br | CH₂CF₂H | |
| 68 | CH₂CH₃ | Br | CH(CH₃)CF₃ | oil |
| 69 | CH₂CH₃ | Br | CH(CH₃)CF₂H | |
| 70 | CH₂CH₃ | Br | CH(CF₃)CF₃ | |
| 71 | CH₂CH₃ | Br | CF(CF₃)CF₃ | |
| 72 | CH₂CH₃ | Br | CH(CF₂H)CF₃ | |
| 73 | CH₂CH₃ | Br | CH(CF₂H)CF₂H | |
| 74 | CH₂CH₃ | Br | CF(CH₃)CF₃ | |
| 75 | CH₂CH₃ | Br | CF(CF₂H)CH₃ | |
| 76 | CH₂CH₃ | Br | CH₂CH₂CF₃ | oil |
| 77 | CH₂CH₃ | Br | CF₂CF₂CF₃ | |
| 78 | CH₂CH₃ | Br | CH₂CF₂CF₃ | |
| 79 | CH₂CH₃ | Br | CH(F)CF₂CF₃ | |
| 80 | CH₂CH₃ | Br | CF₂CF₂CF₂CF₃ | |
| 81 | CH₂CH₃ | Br | CH₂CF₂CF₂CF₃ | |
| 82 | CH₂CH₃ | Br | CH₂CH₂CF₂CF₃ | |
| 83 | CH₂CH₃ | Br | CH₂CH₂CH₂CF₃ | |
| 84 | CH₂CH₃ | Br | CH(CF₃)CH₂CH₃ | oil |
| 85 | CH₂CH₃ | Br | CF(CF₃)CH₂CH₃ | |
| 86 | CH₂CH₃ | Br | CF(CH₃)CH₂CH₃ | |
| 87 | CH₂CH₃ | Br | CF(CH₃)CF₂CF₃ | |
| 88 | CH₂CH₃ | Br | CH(CH₃)CF₂CF₃ | |
| 89 | CH₂CH₃ | Br | CH₂CF(CF₃)2 | |
| 90 | CH₂CH₃ | Br | CF(CF₃)CF₂CF₃ | |
| 91 | CH₂CH₃ | Br | CH(CF₃)CF₂CF₃ | |
| 92 | CH₂CH₃ | Br | CH(CF₂H)CH₂CH₃ | |
| 93 | CH₂CH₃ | Br | CH(CF₂H)CF₂CF₃ | |
| 94 | CH₂CH₃ | Cl | CF₂CF₃ | |
| 95 | CH₂CH₃ | Cl | CH₂CF₃ | oil |
| 96 | CH₂CH₃ | Cl | CH(F)CF₂H | oil |
| 97 | CH₂CH₃ | Cl | CH(F)CF₃ | oil |
| 98 | CH₂CH₃ | Cl | CH(F)C(Cl)F₂ | oil |
| 99 | CH₂CH₃ | Cl | CH₂CF₂H | oil |
| 100 | CH₂CH₃ | Cl | CH(CH₃)CF₃ | $n^{21}_D = 1.5046$ |
| 101 | CH₂CH₃ | Cl | CH(CH₃)CF₂H | oil |
| 102 | CH₂CH₃ | Cl | CH(CF₃)CF₃ | oil |
| 103 | CH₂CH₃ | Cl | CF(CF₃)CF₃ | |
| 104 | CH₂CH₃ | Cl | CH(CF₂H)CF₃ | oil |
| 105 | CH₂CH₃ | Cl | CH(CF₂H)CF₂H | |
| 106 | CH₂CH₃ | Cl | CF(CH₃)CF₃ | |
| 107 | CH₂CH₃ | Cl | CF(CF₂H)CH₃ | |
| 108 | CH₂CH₃ | Cl | CH₂CH₂CF₃ | oil |
| 109 | CH₂CH₃ | Cl | CF₂CF₂CF₃ | |
| 110 | CH₂CH₃ | Cl | CH₂CF₂CF₃ | |
| 111 | CH₂CH₃ | Cl | CH(F)CF₂CF₃ | |
| 112 | CH₂CH₃ | Cl | CF₂CF₂CF₂CF₃ | |
| 113 | CH₂CH₃ | Cl | CH₂CF₂CF₂CF₃ | oil |
| 114 | CH₂CH₃ | Cl | CH₂CH₂CF₂CF₃ | oil |
| 115 | CH₂CH₃ | Cl | CH₂CH₂CH₂CHF₂ | oil |

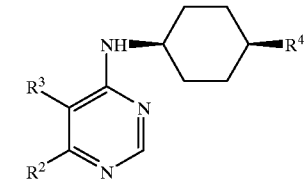

| Ex No | R² | R³ | R⁴ | Physical data |
|---|---|---|---|---|
| 116 | CH₂CH₃ | Cl | CH(CF₃)CH₂CH₃ | oil |
| 117 | CH₂CH₃ | Cl | CF(CF₃)CH₂CH₃ | |
| 118 | CH₂CH₃ | Cl | CF(CH₃)CH₂CH₃ | |
| 119 | CH₂CH₃ | Cl | CF(CH₃)CF₂CF₃ | |
| 120 | CH₂CH₃ | Cl | CH(CH₃)CF₂CF₃ | |
| 121 | CH₂CH₃ | Cl | CH₂CF(CF₃)2 | |
| 122 | CH₂CH₃ | Cl | CF(CF₃)CF₂CF₃ | |
| 123 | CH₂CH₃ | Cl | CH(CF₃)CF₂CF₃ | |
| 124 | CH₂CH₃ | Cl | CH(CF₂H)CH₂CH₃ | |
| 125 | CH₂CH₃ | Cl | CH(CF₂H)CF₂CF₃ | |
| 126 | CH₂CH₃ | CH=CH₂ | CF₂CF₃ | |
| 127 | CH₂CH₃ | CH=CH₂ | CH₂CF₃ | |
| 128 | CH₂CH₃ | CH=CH₂ | CH(F)CF₂H | |
| 129 | CH₂CH₃ | CH=CH₂ | CH(F)CF₃ | |
| 130 | CH₂CH₃ | CH=CH₂ | CH₂CF₂H | |
| 131 | CH₂CH₃ | CH=CH₂ | CH(CH₃)CF₃ | |
| 132 | CH₂CH₃ | CH=CH₂ | CH(CH₃)CF₂H | |
| 133 | CH₂CH₃ | CH=CH₂ | CH(CF₃)CF₃ | |
| 134 | CH₂CH₃ | CH=CH₂ | CF(CF₃)CF₃ | |
| 135 | CH₂CH₃ | CH=CH₂ | CH(CF₂H)CF₃ | |
| 136 | CH₂CH₃ | CH=CH₂ | CH(CF₂H)CF₂H | |
| 137 | CH₂CH₃ | CH=CH₂ | CF(CH₃)CF₃ | |
| 138 | CH₂CH₃ | CH=CH₂ | CF(CF₂H)CH₃ | |
| 139 | CH₂CH₃ | CH=CH₂ | CH₂CH₂CF₃ | |
| 140 | CH₂CH₃ | CH=CH₂ | CF₂CF₂CF₃ | |
| 141 | CH₂CH₃ | CH=CH₂ | CH₂CF₂CF₃ | |
| 142 | CH₂CH₃ | CH=CH₂ | CH(F)CF₂CF₃ | |
| 143 | CH₂CH₃ | CH=CH₂ | CF₂CF₂CF₂CF₃ | |
| 144 | CH₂CH₃ | CH=CH₂ | CH₂CF₂CF₂CF₃ | |
| 145 | CH₂CH₃ | CH=CH₂ | CH₂CH₂CF₂CF₃ | |
| 146 | CH₂CH₃ | CH=CH₂ | CH₂CH₂CH₂CF₃ | |
| 147 | CH₂CH₃ | CH=CH₂ | CH(CF₃)CH₂CH₃ | |
| 148 | CH₂CH₃ | CH=CH₂ | CF(CF₃)CH₂CH₃ | |
| 49 | CH₂CH₃ | CH=CH₂ | CF(CH₃)CH₂CH₃ | |
| 150 | CH₂CH₃ | CH=CH₂ | CF(CH₃)CF₂CF₃ | |
| 151 | CH₂CH₃ | CH=CH₂ | CH(CH₃)CF₂CF₃ | |
| 152 | CH₂CH₃ | CH=CH₂ | CH₂CF(CF₃)₂ | |
| 153 | CH₂CH₃ | CH=CH₂ | CF(CF₃)CF₂CF₃ | |
| 154 | CH₂CH₃ | CH=CH₂ | CH(CF₃)CF₂CF₃ | |
| 155 | CH₂CH₃ | CH=CH₂ | CH(CF₂H)CH₂CH₃ | |
| 156 | CH₂CH₃ | CH=CH₂ | CH(CF₂H)CF₂CF₃ | |
| 157 | CH₂CH₃ | CN | CF₂CF₃ | |
| 158 | CH₂CH₃ | CN | CH₂CF₃ | |
| 159 | CH₂CH₃ | CN | CH(F)CF₂H | |
| 160 | CH₂CH₃ | CN | CH(F)CF₃ | |
| 161 | CH₂CH₃ | CN | CH₂CF₂H | |
| 162 | CH₂CH₃ | CN | CH(CH₃)CF₃ | m.p. 56° C. |
| 163 | CH₂CH₃ | CN | CH(CH₃)CF₂H | |
| 164 | CH₂CH₃ | CN | CH(CF₃)CF₃ | |
| 165 | CH₂CH₃ | CN | CF(CF₃)CF₃ | |
| 166 | CH₂CH₃ | CN | CH(CF₂H)CF₃ | |
| 167 | CH₂CH₃ | CN | CH(CF₂H)CF₂H | |
| 168 | CH₂CH₃ | CN | CF(CH₃)CF₃ | |
| 169 | CH₂CH₃ | CN | CF(CF₂H)CH₃ | |
| 170 | CH₂CH₃ | CN | CH₂CH₂CF₃ | m.p. 81-2° C. |
| 171 | CH₂CH₃ | CN | CF₂CF₂CF₃ | |
| 172 | CH₂CH₃ | CN | CH₂CF₂CF₃ | |
| 173 | CH₂CH₃ | CN | CH(F)CF₂CF₃ | |
| 174 | CH₂CH₃ | CN | CF₂CF₂CF₂CF₃ | |
| 175 | CH₂CH₃ | CN | CH₂CF₂CF₂CF₃ | |
| 176 | CH₂CH₃ | CN | CH₂CH₂CF₂CF₃ | |
| 177 | CH₂CH₃ | CN | CH₂CH₂CH₂CF₃ | |
| 178 | CH₂CH₃ | CN | CH(CF₃)CH₂CH₃ | |
| 179 | CH₂CH₃ | CN | CF(CF₃)CH₂CH₃ | |
| 180 | CH₂CH₃ | CN | CF(CH₃)CH₂CH₃ | |
| 181 | CH₂CH₃ | CN | CF(CH₃)CF₂CF₃ | |

TABLE 1-continued

[Structure: cyclohexyl-NH attached to pyrimidine ring with R³ at position 5, R² at position 6, and R⁴ on cyclohexyl]

| Ex No | R² | R³ | R⁴ | Physical data |
|---|---|---|---|---|
| 182 | $CH_2CH_3$ | CN | $CH(CH_3)CF_2CF_3$ | |
| 183 | $CH_2CH_3$ | CN | $CH_2CF(CF_3)2$ | |
| 184 | $CH_2CH_3$ | CN | $CF(CF_3)CF_2CF_3$ | |
| 185 | $CH_2CH_3$ | CN | $CH(CF_3)CF_2CF_3$ | |
| 186 | $CH_2CH_3$ | CN | $CH(CF_2H)CH_2CH_3$ | |
| 187 | $CH_2CH_3$ | CN | $CH(CF_2H)CF_2CF_3$ | |
| 188 | $CH_2CH_3$ | F | $CF_2CF_3$ | |
| 189 | $CH_2CH_3$ | F | $CH_2CF_3$ | |
| 190 | $CH_2CH_3$ | F | $CH(F)CF_2H$ | |
| 191 | $CH_2CH_3$ | F | $CH(F)CF_3$ | |
| 192 | $CH_2CH_3$ | F | $CH_2CF_2H$ | |
| 193 | $CH_2CH_3$ | F | $CH(CH_3)CF_3$ | m.p. 76° C. |
| 194 | $CH_2CH_3$ | F | $CH(CH_3)CF_2H$ | |
| 195 | $CH_2CH_3$ | F | $CH(CF_3)CF_3$ | |
| 196 | $CH_2CH_3$ | F | $CF(CF_3)CF_3$ | |
| 197 | $CH_2CH_3$ | F | $CH(CF_2H)CF_3$ | |
| 198 | $CH_2CH_3$ | F | $CH(CF_2H)CF_2H$ | |
| 199 | $CH_2CH_3$ | F | $CF(CH_3)CF_3$ | |
| 200 | $CH_2CH_3$ | F | $CF(CF_2H)CH_3$ | |
| 201 | $CH_2CH_3$ | F | $CH_2CH_2CF_3$ | oil |
| 202 | $CH_2CH_3$ | F | $CF_2CF_2CF_3$ | |
| 203 | $CH_2CH_3$ | F | $CH_2CF_2CF_3$ | |
| 204 | $CH_2CH_3$ | F | $CH(F)CF_2CF_3$ | |
| 205 | $CH_2CH_3$ | F | $CF_2CF_2CF_2CF_3$ | |
| 206 | $CH_2CH_3$ | F | $CH_2CF_2CF_2CF_3$ | |
| 207 | $CH_2CH_3$ | F | $CH_2CH_2CF_2CF_3$ | |
| 208 | $CH_2CH_3$ | F | $CH_2CH_2CH_2CF_3$ | |
| 209 | $CH_2CH_3$ | F | $CH(CF_3)CH_2CH_3$ | |
| 210 | $CH_2CH_3$ | F | $CF(CF_3)CH_2CH_3$ | |
| 211 | $CH_2CH_3$ | F | $CF(CH_3)CH_2CH_3$ | |
| 212 | $CH_2CH_3$ | F | $CF(CH_3)CF_2CF_3$ | |
| 213 | $CH_2CH_3$ | F | $CH(CH_3)CF_2CF_3$ | |
| 214 | $CH_2CH_3$ | F | $CH_2CF(CF_3)2$ | |
| 215 | $CH_2CH_3$ | F | $CF(CF_3)CF_2CF_3$ | |
| 216 | $CH_2CH_3$ | F | $CH(CF_3)CF_2CF_3$ | |
| 217 | $CH_2CH_3$ | F | $CH(CF_2H)CH_2CH_3$ | |
| 218 | $CH_2CH_3$ | F | $CH(CF_2H)CF_2CF_3$ | |
| 219 | $CH_2CH_3$ | C≡CH | $CF_2CF_3$ | |
| 220 | $CH_2CH_3$ | C≡CH | $CH_2CF_3$ | |
| 221 | $CH_2CH_3$ | C≡CH | $CH(F)CF_2H$ | |
| 222 | $CH_2CH_3$ | C≡CH | $CH(F)CF_3$ | |
| 223 | $CH_2CH_3$ | C≡CH | $CH_2CF_2H$ | |
| 224 | $CH_2CH_3$ | C≡CH | $CH(CH_3)CF_3$ | m.p. 56° C. |
| 225 | $CH_2CH_3$ | C≡CH | $CH(CH_3)CF_2H$ | |
| 226 | $CH_2CH_3$ | C≡CH | $CH(CF_3)CF_3$ | |
| 227 | $CH_2CH_3$ | C≡CH | $CF(CF_3)CF_3$ | |
| 228 | $CH_2CH_3$ | C≡CH | $CH(CF_2H)CF_3$ | |
| 229 | $CH_2CH_3$ | C≡CH | $CH(CF_2H)CF_2H$ | |
| 230 | $CH_2CH_3$ | C≡CH | $CF(CH_3)CF_3$ | |
| 231 | $CH_2CH_3$ | C≡CH | $CF(CF_2H)CH_3$ | |
| 232 | $CH_2CH_3$ | C≡CH | $CH_2CH_2CF_3$ | oil |
| 233 | $CH_2CH_3$ | C≡CH | $CF_2CF_2CF_3$ | |
| 234 | $CH_2CH_3$ | C≡CH | $CH_2CF_2CF_3$ | |
| 235 | $CH_2CH_3$ | C≡CH | $CH(F)CF_2CF_3$ | |
| 236 | $CH_2CH_3$ | C≡CH | $CF_2CF_2CF_2CF_3$ | |
| 237 | $CH_2CH_3$ | C≡CH | $CH_2CF_2CF_2CF_3$ | |
| 238 | $CH_2CH_3$ | C≡CH | $CH_2CH_2CF_2CF_3$ | |
| 239 | $CH_2CH_3$ | C≡CH | $CH_2CH_2CH_2CF_3$ | |
| 240 | $CH_2CH_3$ | C≡CH | $CH(CF_3)CH_2CH_3$ | |
| 241 | $CH_2CH_3$ | C≡CH | $CF(CF_3)CH_2CH_3$ | |
| 242 | $CH_2CH_3$ | C≡CH | $CF(CH_3)CH_2CH_3$ | |
| 243 | $CH_2CH_3$ | C≡CH | $CF(CH_3)CF_2CF_3$ | |
| 244 | $CH_2CH_3$ | C≡CH | $CH(CH_3)CF_2CF_3$ | |
| 245 | $CH_2CH_3$ | C≡CH | $CH_2CF(CF_3)_2$ | |
| 246 | $CH_2CH_3$ | C≡CH | $CF(CF_3)CF_2CF_3$ | |
| 247 | $CH_2CH_3$ | C≡CH | $CH(CF_3)CF_2CF_3$ | |
| 248 | $CH_2CH_3$ | C≡CH | $CH(CF_2H)CH_2CH_3$ | |
| 249 | $CH_2CH_3$ | C≡CH | $CH(CF_2H)CF_2CF_3$ | |
| 250 | $CH_2CH_3$ | H | $CF_2CF_3$ | |
| 251 | $CH_2CH_3$ | H | $CH_2CF_3$ | |
| 252 | $CH_2CH_3$ | H | $CH(F)CF_2H$ | |
| 253 | $CH_2CH_3$ | H | $CH(F)CF_3$ | |
| 254 | $CH_2CH_3$ | H | $CH_2CF_2H$ | |
| 255 | $CH_2CH_3$ | H | $CH(CH_3)CF_3$ | m.p. 83–86° C. |
| 256 | $CH_2CH_3$ | H | $CH(CH_3)CF_2H$ | oil |
| 257 | $CH_2CH_3$ | H | $CH(CF_3)CF_3$ | |
| 258 | $CH_2CH_3$ | H | $CF(CF_3)CF_3$ | |
| 259 | $CH_2CH_3$ | H | $CH(CF_2H)CF_3$ | |
| 260 | $CH_2CH_3$ | H | $CH(CF_2H)CF_2H$ | |
| 261 | $CH_2CH_3$ | H | $CF(CH_3)CF_3$ | |
| 262 | $CH_2CH_3$ | H | $CF(CF_2H)CH_3$ | |
| 263 | $CH_2CH_3$ | H | $CH_2CH_2CF_3$ | oil |
| 264 | $CH_2CH_3$ | H | $CF_2CF_2CF_3$ | |
| 265 | $CH_2CH_3$ | H | $CH_2CF_2CF_3$ | |
| 266 | $CH_2CH_3$ | H | $CH(F)CF_2CF_3$ | |
| 267 | $CH_2CH_3$ | H | $CF_2CF_2CF_2CF_3$ | |
| 268 | $CH_2CH_3$ | H | $CH_2CF_2CF_2CF_3$ | |
| 269 | $CH_2CH_3$ | H | $CH_2CH_2CF_2CF_3$ | |
| 270 | $CH_2CH_3$ | H | $CH_2CH_2CH_2CF_3$ | |
| 271 | $CH_2CH_3$ | H | $CH(CF_3)CH_2CH_3$ | |
| 272 | $CH_2CH_3$ | H | $CF(CF_3)CH_2CH_3$ | |
| 273 | $CH_2CH_3$ | H | $CF(CH_3)CH_2CH_3$ | |
| 274 | $CH_2CH_3$ | H | $CF(CH_3)CF_2CF_3$ | |
| 275 | $CH_2CH_3$ | H | $CH(CH_3)CF_2CF_3$ | |
| 276 | $CH_2CH_3$ | H | $CH_2CF(CF_3)_2$ | |
| 277 | $CH_2CH_3$ | H | $CF(CF_3)CF_2CF_3$ | |
| 278 | $CH_2CH_3$ | H | $CH(CF_3)CF_2CF_3$ | |
| 279 | $CH_2CH_3$ | H | $CH(CF_2H)CH_2CH_3$ | |
| 280 | $CH_2CH_3$ | H | $CH(CF_2H)CF_2CF_3$ | |
| 281 | $CH_3$ | H | $CF_2CF_3$ | |
| 282 | $CH_3$ | H | $CH_2CF_3$ | |
| 283 | $CH_3$ | H | $CH(F)CF_2H$ | |
| 284 | $CH_3$ | H | $CH(F)CF_3$ | |
| 285 | $CH_3$ | H | $CH_2CF_2H$ | |
| 286 | $CH_3$ | H | $CH(CH_3)CF_3$ | m.p.: 102–104° C. |
| 287 | $CH_3$ | H | $CH(CH_3)CF_2H$ | |
| 288 | $CH_3$ | H | $CH(CF_3)CF_3$ | |
| 289 | $CH_3$ | H | $CF(CF_3)CF_3$ | |
| 290 | $CH_3$ | H | $CH(CF_2H)CF_3$ | |
| 291 | $CH_3$ | H | $CH(CF_2H)CF_2H$ | |
| 292 | $CH_3$ | H | $CF(CH_3)CF_3$ | |
| 293 | $CH_3$ | H | $CF(CF_2H)CH_3$ | |
| 294 | $CH_3$ | H | $CH_2CH_2CF_3$ | oil |
| 295 | $CH_3$ | H | $CF_2CF_2CF_3$ | |
| 296 | $CH_3$ | H | $CH_2CF_2CF_3$ | |
| 297 | $CH_3$ | H | $CH(F)CF_2CF_3$ | |
| 298 | $CH_3$ | H | $CF_2CF_2CF_2CF_3$ | |
| 299 | $CH_3$ | H | $CH_2CF_2CF_2CF_3$ | |
| 300 | $CH_3$ | H | $CH_2CH_2CF_2CF_3$ | |
| 301 | $CH_3$ | H | $CH_2CH_2CH_2CF_3$ | |
| 302 | $CH_3$ | H | $CH(CF_3)CH_2CH_3$ | |
| 303 | $CH_3$ | H | $CF(CF_3)CH_2CH_3$ | |
| 304 | $CH_3$ | H | $CF(CH_3)CH_2CH_3$ | |
| 305 | $CH_3$ | H | $CF(CH_3)CF_2CF_3$ | |
| 306 | $CH_3$ | H | $CH(CH_3)CF_2CF_3$ | |
| 307 | $CH_3$ | H | $CH_2CF(CF_3)2$ | |
| 308 | $CH_3$ | H | $CF(CF_3)CF_2CF_3$ | |
| 309 | $CH_3$ | H | $CH(CF_3)CF_2CF_3$ | |
| 310 | $CH_3$ | H | $CH(CF_2H)CH_2CH_3$ | |
| 311 | $CH_3$ | H | $CH(CF_2H)CF_2CF_3$ | |
| 312 | $CH_2CH_3$ | Cl | $CF(CF_2H)CH_3$ | x HCl |

TABLE 1-continued

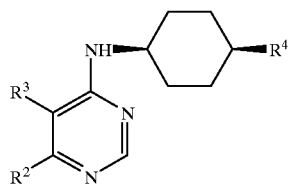

| Ex No | $R^2$ | $R^3$ | $R^4$ | Physical data |
|---|---|---|---|---|
| 313 | $CH_2CH_3$ | Cl | $CH_2CH_2CF_3$ | x HCl |
| 314 | $CH_2CH_3$ | Cl | $CH(CH_3)CF_3$ | x HCl |
| 315 | $CH_2CH_3$ | Cl | $CF(CF_2H)CH_3$ | x $HNO_3$ |
| 316 | $CH_2CH_3$ | Cl | $CH_2CH_2CF_3$ | x $HNO_3$ |
| 317 | $CH_2CH_3$ | Cl | $CH(CH_3)CF_3$ | x $HNO_3$ |
| 318 | $CH_2CH_3$ | Cl | $CF(CF_2H)CH_3$ | x $CH_3SO_3H$ |
| 319 | $CH_2CH_3$ | Cl | $CH_2CH_2CF_3$ | x $CH_3SO_3H$ |
| 320 | $CH_2CH_3$ | Cl | $CH(CH_3)CF_3$ | x $CH_3SO_3H$ |
| 321 | $CH_2CH_3$ | Cl | $CF(CF_2H)CH_3$ | x $H_2C_2O_4$ |
| 322 | $CH_2CH_3$ | Cl | $CH_2CH_2CF_3$ | x $H_2C_2O_4$ |
| 323 | $CH_2CH_3$ | Cl | $CH(CH_3)CF_3$ | x $H_2C_2O_4$ |
| 324 | $CH_2CH_3$ | Cl | $CF(CF_2H)CH_3$ | x p-toluene-sulfonic acid |
| 325 | $CH_2CH_3$ | Cl | $CH_2CH_2CF_3$ | x p-toluene-sulfonic acid |
| 326 | $CH_2CH_3$ | Cl | $CH(CH_3)CF_3$ | x p-toluene-sulfonic acid |
| 327 | $CH_2CH_3$ | Cl | $CF(CF_2H)CH_3$ | x (1s)-(+)-camphorsulfonic acid |
| 328 | $CH_2CH_3$ | Cl | $CH_2CH_2CF_3$ | x (1s)-(+)-camphorsulfonic acid |
| 329 | $CH_2CH_3$ | Cl | $CH(CH_3)CF_3$ | x (1s)-(+)-camphorsulfonic acid |
| 330 | $CH_2CH_3$ | $OCH_3$ | $CH(CH_3)CF_3$ | oil |
| 331 | $CH_2CH_3$ | $OCH_3$ | $CH_2CH_2CF_3$ | gum |
| 332 | $(CH_2)_2CH_3$ | Cl | $CH(CH_3)CF_3$ | oil |
| 333 | $CH_2CH_3$ | Cl | $CH_2CH_2CF_2H$ | oil |

TABLE 1-continued

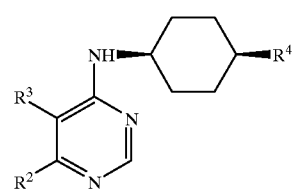

| Ex No | $R^2$ | $R^3$ | $R^4$ | Physical data |
|---|---|---|---|---|
| 334 | $CH_2CH_3$ | Cl | $CH_2CH_2CH_2CF_2H$ | oil |
| 335 | $CH_2OCH_3$ | H | $CH_2CH_2CF_3$ | oil |
| 336 | $CH_2OCH_3$ | Cl | $CH_2CH_2CF_3$ | oil |
| 337 | $CH_2OCH_3$ | Br | $CH_2CH_2CF_3$ | oil |
| 338 | $CH_2OCH_3$ | $OCH_3$ | $CH_2CH(OCH_3)CF_3$ | oil |
| 339 | $CH_2CH_3$ | F | $CH=CHCF_3$ | |
| 340 | $CH_2CH_3$ | Cl | $CH=CHCF_3$ | |
| 341 | $CH_2CH_3$ | Br | $CH=CHCF_3$ | |
| 342 | $CH_2CH_3$ | I | $CH=CHCF_3$ | |
| 343 | $CH_2CH_3$ | CN | $CH=CHCF_3$ | |
| 344 | $CH_2CH_3$ | $OCH_3$ | $CH=CHCF_3$ | oil |
| 345 | $CH_2CH_3$ | $CH=CH_2$ | $CH=CHCF_3$ | |
| 346 | $CH_2CH_3$ | $C\equiv CH$ | $CH=CHCF_3$ | |
| 347 | $CH_2OCH_3$ | $OCH_3$ | $CH=CHCF_3$ | |
| 348 | $CHFCH_3$ | Cl | $CH=CHCF_3$ | |
| 349 | $CHFCH_3$ | Cl | $C\equiv CCF_3$ | |
| 350 | $CH_2CH_3$ | F | $C\equiv CCF_3$ | |
| 351 | $CH_2CH_3$ | Cl | $C\equiv CCF_3$ | |
| 352 | $CH_2CH_3$ | Br | $C\equiv CCF_3$ | |
| 353 | $CH_2CH_3$ | I | $C\equiv CCF_3$ | |
| 354 | $CH_2CH_3$ | CN | $C\equiv CCF_3$ | |
| 355 | $CH_2CH_3$ | $OCH_3$ | $C\equiv CCF_3$ | |
| 356 | $CH_2CH_3$ | $CH=CH_2$ | $C\equiv CCF_3$ | |
| 357 | $CH_2CH_3$ | $C\equiv CH$ | $C\equiv CCF_3$ | |
| 358 | $CH_2OCH_3$ | $OCH_3$ | $C\equiv CCF_3$ | |
| 359 | $CHFCH_3$ | Cl | $CH_2CH_2CF_3$ | |
| 360 | $CHFCH_3$ | Cl | $CH(CH_3)CF_3$ | |

TABLE 2

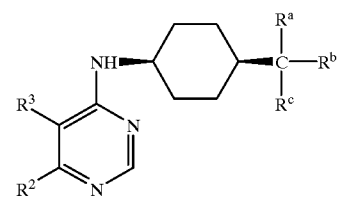

| Ex No | $R^2$ | $R^3$ | $R^a$ | $R^b$ | $R^c$ | Physical data |
|---|---|---|---|---|---|---|
| 500 | $C_2H_5$ | Cl | H | $CF_3$ | $OCH_3$ | oil |
| 501 | $C_2H_5$ | Cl | H | $CF_3$ | $OCH_3$ | methane-sulfonate salt m.p. 101–103° C. |
| 502 | $C_2H_5$ | Cl | H | $CF_3$ | $OCH_3$ | camphor-sulfonate salt m.p. 75–77° C. |
| 503 | $C_2H_5$ | F | H | $CF_3$ | $OCH_3$ | oil |
| 504 | $C_2H_5$ | Br | H | $CF_3$ | $OCH_3$ | oil |

TABLE 2-continued

| Ex No | $R^2$ | $R^3$ | $R^a$ | $R^b$ | $R^c$ | Physical data |
|---|---|---|---|---|---|---|
| 505 | $C_2H_5$ | I | H | $CF_3$ | $OCH_3$ | oil |
| 506 | $C_2H_5$ | C≡CH | H | $CF_3$ | $OCH_3$ | oil |
| 507 | $C_2H_5$ | CH=$CH_2$ | H | $CF_3$ | $OCH_3$ | oil |
| 508 | $C_2H_5$ | Br | H | $CF_3$ | $OCH_3$ | methane-sulfonate m.p. 101–103° C. |
| 509 | $C_2H_5$ | Br | H | $CF_3$ | $OCH_3$ | camphor-sulfonate m.p. 75–77° C. |
| 510 | $CH_2OCH_3$ | Br | H | $CF_3$ | $OCH_3$ | oil |
| 511 | $CH_3$ | Cl | H | $CF_3$ | $OCH_3$ | oil |
| 512 | $CH_3$ | H | H | $CF_3$ | $OCH_3$ | oil |
| 513 | $C_2H_5$ | H | H | $CF_3$ | $OCH_3$ | oil |
| 514 | $CHFCH_3$ | Cl | H | $CF_3$ | $OCH_3$ | |
| 515 | $C_2H_5$ | Cl | $CH_3$ | $CF_3$ | $OCH_3$ | oil |
| 516 | $CH_2OCH_3$ | $OCH_3$ | $CH_3$ | $CF_3$ | $OCH_3$ | oil |
| 517 | $C_2H_5$ | Cl | H | $CF_3$ | $OC_2H_5$ | oil |
| 518 | $CH_2OCH_2$ | $OCH_3$ | H | $CF_3$ | $OC_2H_5$ | oil |
| 519 | $C_2H_5$ | Br | H | $CF_3$ | $OC_2H_5$ | oil |
| 520 | $C_2H_5$ | Cl | $CH_3$ | $CF_3$ | $OC_2H_5$ | oil |
| 521 | $C_2H_5$ | Cl | H | $CF_3$ | $O(CH_2)_2CH_3$ | oil |
| 522 | $C_2H_5$ | Br | H | $CF_3$ | $O(CH_2)_2CH_3$ | oil |
| 523 | $CH_2OCH_3$ | $OCH_3$ | H | $CF_3$ | $O(CH_2)_2CH_3$ | oil |
| 524 | $C_2H_5$ | Cl | H | $CF_3$ | $O(CH_2)_3CH_3$ | oil |
| 525 | $C_2H_5$ | Br | H | $CF_3$ | $O(CH_2)_3CH_3$ | oil |
| 526 | $CH_2OCH_3$ | $OCH_3$ | H | $CF_3$ | $O(CH_2)_3CH_3$ | oil |
| 527 | $C_2H_5$ | Cl | H | $CF_3$ | $OCH(CH_3)C_2H_5$ | oil |
| 528 | $C_2H_5$ | Cl | H | $CF_3$ | $OCH(CH_3)_2$ | oil |
| 529 | $C_2H_5$ | Cl | H | $CF_3$ | $OCH_2CH=CH_2$ | |
| 530 | $C_2H_5$ | Cl | H | $CF_3$ | $OCH_2C≡CH$ | oil |
| 531 | $C_2H_5$ | Br | H | $CF_3$ | $OCH_2C≡CH$ | oil |
| 532 | $CH_2OCH_3$ | $OCH_2$ | H | $CF_3$ | $OCH_2C≡CH$ | oil |
| 533 | $CH_2OCH_3$ | $OCH_3$ | H | $CF_3$ | $OCH_2CN$ | oil |
| 534 | $C_2H_5$ | Cl | H | $CF_3$ | $OCH_2CN$ | oil |
| 535 | $C_2H_5$ | Br | H | $CF_3$ | $OCH_2CN$ | oil |
| 536 | $C_2H_5$ | Cl | F | F | $CH_2OCH_3$ | |
| 537 | $C_2H_5$ | Cl | F | F | $CH_2OC_2H_5$ | |
| 538 | $C_2H_5$ | Cl | F | F | $CH_2OCH_2CH=CH_2$ | |
| 539 | $C_2H_5$ | Cl | F | F | $CH_2OCH_2C≡CH$ | |
| 540 | $C_2H_5$ | Cl | F | F | $CH_3$ | |
| 541 | $C_2H_5$ | Cl | F | F | $CH_2F$ | |
| 542 | $C_2H_5$ | Cl | F | F | $C_2H_5$ | |
| 543 | $C_2H_5$ | Cl | F | F | $CHFCH_3$ | |
| 544 | $C_2H_5$ | Cl | H | H | $CHFCF_3$ | |
| 545 | $C_2H_5$ | Cl | $CH_2F$ | H | $CH_2F$ | oil |
| 546 | $C_2H_5$ | Cl | $CH_2F$ | F | $CH_2F$ | |
| 547 | $C_2H_5$ | Cl | $CH_2F$ | $CH_3$ | $CH_2F$ | |
| 548 | $C_2H_5$ | Cl | $CH_2F$ | H | $CF_3$ | |
| 549 | $C_2H_5$ | Cl | $CH_2F$ | $CH_2F$ | $CH_3$ | |
| 550 | $C_2H_5$ | Cl | F | $CH_2F$ | $CH_2F$ | |
| 551 | $C_2H_5$ | Cl | $CH_3$ | $CH_3$ | $CF_3$ | |
| 552 | $C_2H_5$ | Cl | F | H | $(CH_2)_3F$ | |
| 553 | $C_2H_5$ | Cl | F | H | $CHFC_2H_5$ | |
| 554 | $C_2H_5$ | Cl | H | H | $CHFCHFCH_3$ | |
| 555 | $C_2H_5$ | Cl | H | H | $CH_2CHFCF_3$ | |
| 556 | $C_2H_5$ | Cl | $CH_2F$ | $CH_2F$ | $CH_2OCH_2CH_3$ | |
| 557 | $C_2H_5$ | Cl | H | F | $(CH_2)_3F$ | |
| 558 | $C_2H_5$ | Cl | $CH_3$ | $CH_3$ | $CF_3$ | |
| 559 | $C_2H_5$ | Cl | $CH_3$ | $CH_3$ | $CH_2CHF_2$ | |

TABLE 3

| Ex No | R¹ | R² | R³ | Rᵃ | Rᵇ | Rᶜ | Physical data |
|---|---|---|---|---|---|---|---|
| 600 | CH₃ | C₂H₅ | Cl | H | CF₃ | OCH₃ | oil |
| 601 | Cl | C₂H₅ | Cl | H | CF₃ | OCH₃ | oil |
| 602 | CH₃ | C₂H₅ | F | H | CF₃ | OCH₃ | oil |
| 603 | CH₃ | C₂H₅ | H | H | CF₃ | OCH₃ | oil |
| 604 | Cl | C₂H₅ | H | H | CF₃ | OCH₃ | oil |
| 605 | H | CH₃ | OCH₃ | H | CF₃ | OCH₃ | oil |

TABLE 4

| Ex No | R¹ | R² | R³ | R⁴ | Physical data |
|---|---|---|---|---|---|
| 700 | CH₃ | CH₃ | Cl | CH₂CH₂CF₃ | oil |
| 701 | CH₃ | CH₃ | Cl | CH(CH₃)CF₃ | oil |
| 702 | Cl | CH₃ | Cl | CH(CH₃)CF₃ | m.p. 69° C. |
| 703 | Cl | CH₃ | Cl | CH₂CH₂CF₃ | oil |
| 704 | Cl | CH₂CH₃ | Cl | CH(CH₃)CF₃ | oil |
| 705 | Cl | CH₂CH₃ | Cl | CH(CH₃)CF₂H | oil |
| 706 | CH₃ | CH₂CH₃ | Cl | CH(CH₃)CF₃ | oil |
| 707 | CH₃ | CH₂CH₃ | Cl | CH₂CH₂CF₃ | oil |
| 708 | Cl | CH₂CH₃ | Cl | CH₂CH₂CF₃ | oil |
| 709 | CH₃ | CH₂OCH₃ | OCH₃ | CH₂CH₂CF₃ | oil |
| 710 | Cl | CH₂OCH₃ | OCH₃ | CH₂CH₂CF₃ | oil |
| 711 | CH₃ | CH₂CH₃ | Br | CH₂CH₂CF₃ | oil |
| 712 | CH₃ | CH₂CH₃ | CN | CH(CH₃)CF₃ | m.p. 92–5° C. |
| 713 | CH₃ | CH₂CH₃ | F | CH₂CH₂CF₃ | oil |
| 714 | CH₃ | CH₂CH₃ | F | CH(CH₃)CF₃ | m.p. 98° C. |
| 715 | CH₃ | CH₂CH₃ | C CH | CH(CH₃)CF₃ | oil |
| 716 | CH₃ | CH₂CH₃ | H | CH(CH₃)CF₃ | m.p. 114–5° C. |
| 717 | CH₃ | CH₂CH₃ | H | CH₂CH₂CF₃ | oil |
| 718 | Cl | CH₃ | H | CH(CH₃)CF₃ | m.p. 163° C. |
| 719 | CH₃ | CH₂OCH₃ | H | CH₂CH₂CF₃ | oil |
| 720 | Cl | CH₂OCH₃ | H | CH₂CH₂CF₃ | oil |
| 721 | CH₃ | CH₂CH₃ | OCH₃ | CH₂CH₂CF₃ | oil |
| 722 | Cl | CH₂CH₃ | OCH₃ | CH₂CH₂CF₃ | oil |
| 723 | Cl | CH₂OCH₃ | Cl | CH₂CH₂CF₃ | oil |
| 724 | CH₃ | CH₂OCH₃ | Cl | CH₂CH₂CF₃ | oil |
| 725 | CH₃ | CH₂OCH₃ | Br | CH₂CH₂CF₃ | oil |
| 726 | Cl | CH₂OCH₃ | Br | CH₂CH₂CF₃ | oil |

BIOLOGICAL EXAMPLES

Use as a Fungicide

Example Af

Compounds were assessed for activity against one or more of the following:

*Phytophthora infestans*: late tomato blight
*Plasmopara viticola*: vine downy mildew
*Erysiphe graminis f.* sp. *tritici*: wheat powdery mildew
*Pyricularia oryzae*: rice blast
*Botrytis cinerea*: grey mould Aqueous solutions or dispersions of the compounds at the desired concentration, including a wetting agent, were applied by spray or by drenching the stem base of the test plants, as appropriate. After a given time, plants or plant parts were inoculated with appropriate test pathogens before or after application of the compounds as appropriate, and kept under controlled environmental conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified.

*Phytophthora infestans*
   100, 330
*Plasmopara viticola:*
   37, 84
*Erysiphe graminis f.* sp. *tritici:*
   37, 53
*Pyricularia oryzae*
   101, 330
*Botrytis cinerea*
   53, 84

Use as an Acaricide

Example Aa

Activity Against *Tetranychus urticae* i) Cut stems of bean plants (*Phaseolus vulgaris*) carrying one leaf are transferred into brown glass bottles filled with tap water and subsequently populated with approximately 100 spider mites (*Tetranychus urticae*). The plant leaf and the spider mites are then dipped for 5 seconds into an aqueous solution or dispersion of the formulated compound to be tested. After the formulation has dripped off, plants and mites are kept in a controlled environment chamber (16 hours of light/day, 25° C., 40–60% relative humidity). After 6 days storage, the effect of the preparation on all stages of the spider mites is determined. At a concentration of 300 ppm (based on the content of active compound), compounds of Example Nos. 6, 39, 45, 53, 76, 94–97, 100, 101, 102, 108, 112, 170, 193, 224, 232, 255, 256, 263, 286, 294, 314, 317, 320, 323, 326, 329–334, 337, 338, 500–506, 508–512, 515–526, 530–535, 545, 601, 602, 605, 700, 702, 710, 712, 713, 722 and 725 cause a mortality of 90–100%.

ii) In a similar test, where the leaves and mites are sprayed to run-off instead of dipping, compounds of Examples 37, 68, 84, 100 and 116 cause a mortality of 90–100%.

ii) In a similar test, using a full population of spider mites on the leaves, after 7 days the compound of Example 107 causes a mortality of 90–100%.

Example Ab

Activity Against *Metatetranychus/Panonychus ulmi*

Apple plants (*Malus domesticus*) heavily infested with a full population of fruit tree spider mites (*Metatetranychus/Panonychus ulmi*) are sprayed to runoff point with an aqueous formulated solution or dispersion of the compound to be tested. The mortality among all stages of the mite is determined after 7 days. At a concentration of 300 ppm (based on the content of active compound), the compund of Example No. 107 causes a mortality of 90–100%.

Use as an Insecticide

Example Ia

Activity Against *Aphis fabae*

Broad beans (*Vicia faba*) heavily infested with the black bean aphid (*Aphis fabae*) are sprayed to runoff point with an aqueous solution or dispersion of the formulated compund to be tested. The mortality of the aphids is determined after 3 days. At a concentration of 300 ppm (based on the content of active compound), the compund of Example No. 107 causes a mortality of 90–100%.

Example Ib

Activity Against *Aphis fabae* i) Germinated broad bean seeds (*Vicia faba*) with radicles are transferred into brown glass bottles filled with tap water and subsequently populated with approximately 100 black bean aphids (*Aphis fabae*). Plants and aphids are sprayed to runoff point with an aqueous solution or dispersion of the formulated compound to be tested. After the formulation has dripped off, plants and aphids are kept in a controlled environment chamber (16 hours of light/day, 25° C., 40–60% relative humidity). After 6 days storage, the effect of the compounds on the aphids is determined. At a concentration of 300 ppm (based on the content of active compound), the compounds of Example Nos. 37, 84, 68, 84 and 116 cause a mortality of 90–100%.

ii) In a similar test, where the leaves and aphids are dipped for 5 seconds instead of spraying, compounds of Examples 6, 39, 45, 53, 76, 94–97, 100–102, 108, 112, 170, 193, 232, 286, 294, 314, 317, 320, 323, 326, 329–338, 344, 500–506, 508–10, 515–527, 530–535, 545, 600–2, 605, 700, 701, 704–8, 710–3, 715 and 722–6 cause a mortality of 90–100%.

iii) In a similar test to ii), 4 ml of an aqueous solution or dispersion of the compound is pipetted into the bottle which is filled with water and contains the germinated broad bean seeds with radicles which are then populated with approximately 100 black bean aphids. Compounds of Examples 45, 263, 330, 331, 336, 338, 344, 721 and 724 cause a mortality of 90–100%.

Example Ic

Activity Against *Myzus persicae*

Broad beans or belipepper plants which are heavily infested with the green peach aphid (*Myzus persicae*) are sprayed to runoff point with an aqueous solution or dispersion of the formulated compound to be tested. The mortality of aphids is determined after 3 days. At a concentration of 300 ppm (based on the content of active compound), the compounds of Example Nos. 100, 108, 314, 317, 320, 323, 326 and 329 cause a mortality of 90–100%.

Example Id

Activity Against *Planococcus citri*

Bean plants (*Phaseolus vulgaris*) heavily populated with the common citrus mealy bug (*Planococcus citri*) are sprayed to runoff point with an aqueous solution or dispersion of the formulated compound to be tested. The mortality of the mealy bugs is determined after 7 days. At a concentration of 300 ppm (based on the content of active compound), the compound of Example No. 100 causes a mortality of 90–100%.

Example Ie

Activity Against *Bemisia tabaci*

For oviposition, bean plants (*Phaseolus vulgaris*) are populated for 48 hours with adults of the tobacco whitefly (*Bemisia tabaci*). After the larvae have emerged, the plants are sprayed to runoff point with an aqueous solution or dispersion of the formulated compound to be tested. After 11 days, the larvicidal activity is determined. At a concentration of 300 ppm (based on the content of active compound), the compounds of Example Nos. 100, 108, 314, 317, 320 and 326 show an activity of 90–100%.

Example If

Activity Against *Trialeurodes vaporariorum*

Bean plants (*Phaseolus vulgaris*) are populated with adults of the whitefly (*Trialeurodes vaporariorum*) for 48 hours. After the leaves are covered uniformly with eggs, the plants are sprayed to runoff point with an aqueous solution or dispersion of the formulated compound to be tested. After 11 days (development time for L2–L3 larval stages), the ovicidal and larvicidal effect is determined. At a concentration of 300 ppm (based on the content of active compound), the compounds of Example Nos. 68, 84, 10 and 116 show an activity of 90–100%.

Example Ig

Activity Against *Nilaparvata Iugens* i) Rice seed is germinated on damp cotton wool in growing glasses and, after growing to a stem length of about 8 cm, the leaves are dipped into an aqueous solution or dispersion of the formulated compound to be tested. After the formulation has dripped off, the rice plants treated in this way are introduced into cultivation containers and populated with in each case 10 larvae (L3 stage) of the rice leaf hopper species *Nilaparvata lugens*. After the closed cultivation containers have been kept at 21° C., the mortality of the leaf hopper larvae is determined after 4 days. At a concentration of 300 ppm (based on the content of active compound), the compound of Example No. 107 causes a mortality of 90–100%.

ii) In a similar test, leaves of 12 rice plants having a stem length of 8 cm are dipped for 5 seconds into an aqueous solution or dispersion of the formulated compound to be tested. After the formulation has dripped off, the rice plants treated in this manner are placed in a Petri dish and populated with approximately 20 larvae (L3 stage) of the rice leaf hopper species *Nilaparvata lugens*. The Petri dish is closed and stored in a controlled environment chamber (16 hours of light/day, 25° C., 40–60% relative humidity). After 6 days storage, the mortality of the leaf hopper larvae is determined. At a concentration of 300 ppm (based on the content of active compound), the compounds of Example Nos. 6, 39, 45, 76, 94, 95, 96, 97, 100–2, 108, 112, 170, 193, 224, 232, 255, 256, 286, 294, 314, 317, 320, 323, 326, 329–338, 344, 500–506, 508–511, 515–527, 530–535, 545, 600–2, 605, 700–2, 704–8, 710–3, 715 and 721–6 cause a mortality of 90–100%.

Example Ih

Activity Againt *Nephotettix cincticeps*

In a similar test to Example 1g(i), the compound of Example No. 37 causes 90–100% mortality of of the rice leaf hopper species *Nephotettix cincticeps*.

Example Ii

Activity Against *Musca domestica*

In each case 1 ml of an aqueous-acetone emulsion of the compound to be tested, is applied evenly to the inside of the lid and the bottom of a Petri dish. After the coating has dried, in each case 10 imagoes of the common housefly (*Musca domestica*) are placed into the Petri dish. The dishes are sealed and kept at room temperature and, after 3 hours, the mortality of the flies is determined. At a concentration of 300 ppm (based on the content of active compound), the compounds of Example Nos. 68, 84, 100 and 116 cause a mortality of 90–100%.

Example Ij

Activity Against *Blattella germanica* i) In a similar test to Example Ii, at a concentration of 300 ppm, the compounds of Examples 68, 84, 100 and 107 cause 90–100% of the German cockroach (*Blattella germanica*).

ii) In a similar test, the Petri dish is first covered with filter paper and on top is placed a quarter of a thin baked wafer. One ml of an aqueous solution or dispersion of the formulated compound to be tested is spread on the thin baked wafer. Five L4 larvae of the German cockroach (*Blattella germanica*) are placed in the Petri dish, which is sealed and kept at about 25° C. in a controlled environment chamber. After 6 days, the effect of the compounds on the larvae is determined. At a concentration of 300 ppm (based on the content of active compound), the compounds of Example Nos. 39, 170, 224, 232, 314, 317, 320, 326, 330, 331, 501, 502, 506, 515, 530, 532, 600, 712 and 713 cause a mortality of 90–100% among the larvae.

Example Ik

Activity Against *Heliothis virescens* i) Pieces of filter paper with about 30 24-hour-old eggs of the American tobacco budworm (*Heliothis virescens*) are dipped for 5 seconds into an aqueous solution or dispersion of the formulated compound to be tested and subsequently placed into a Petri dish whose bottom is covered with filter paper and which contains about 5 ml of nutrient medium. A further 200 µl of the aqueous solution are spread over the nutrient medium. The Petri dish is closed and then kept at about 25° C. in a controlled environment chamber. After 6 daysstorage, the effect of the preparation on the eggs and any larvae which may have hatched from these is determined. At a concentration of 300 ppm (based on the content of active compound), compounds of Example Nos. 6, 39, 45, 53, 76, 94–97, 100–102, 108, 112, 170, 193, 224, 232, 255, 256, 263, 294, 314, 317, 320, 323, 326, 329–338, 344, 500–506, 508–511, 515–521, 523, 524, 526, 530–535, 545, 600, 605, 700, 701, 706–8, 710–3, 715 and 722–6 cause a mortality of 90–100%.

ii) In a similar test, ten L3 larvae of the American tobacco budworm (*Heliothis virescens*) are placed into a Petri dish whose bottom is covered with filter paper and which contains about 5 ml of culture medium. Filter paper, culture medium and the larvae employed are then sprayed with an aqueous solution or dispersion of the formulated compound to be tested and the Petri dish is closed with a lid. After 4 days storage at approximately 23° C., the effect of the compounds on the larvae is determined. At a concentration of 300 ppm (based on the content of active compound), the compounds of Example Nos. 37, 68 and 100 cause a mortality of 90–100%.

iii) In a similar test, to ii) above in which larvae are replaced by eggs, after 7 days storage at approximately 23° C., the effect of the preparation on the eggs is determined. At a concentration of 300 ppm (based on the content of active compound), the compounds of Example Nos. 68, 84, 100 and 116 cause a mortality of 90–100% among the eggs.

Example Il

Activity Against *Spodoptera littoralis* i). 10 L2 larvae of the Egyptian cotton worm (*Spodoptera litoralis*) are counted into a small beaker. 200 µl of an aqueous solution or dispersion of the formulated compound to be tested are pipetted into the beaker. The treated larvae are then poured into a Petri dish whose bottom is covered with filter paper and which contains about 5 ml of nutrient and a further 200 µl of the aqueous solution are spread over the culture medium. The Petri dish is closed and then kept at approximately 25° C. in a controlled environment chamber. After 6 days storage, the effect of the preparation on the larvae is determined. At a concentration of 300 ppm (based on the content of active compound), the compounds Example Nos. 6, 38, 39, 45, 53, 76, 94–97, 100–102, 107, 108, 112, 170, 193, 224, 232, 294, 314, 317, 320, 323, 329–331, 333, 334, 336–8, 500–506, 509–511, 515–524, 526, 530–535, 545, 600, 700, 701, 706, 721–722, and 725 cause 90–100% mortality.

ii) In a similar test to Example Ik(ii), but using L4 larvae of the Egyptian cotton worm (*Spodoptera littoralis*) compounds of Example Nos. 37, 68 and 100 cause a mortality of 90–100% among the larvae.

Example Im

Activity Against *Plutella maculipennis*

A leaf of white cabbage is populated with larvae of the diamondback moth (*Plutella maculipennis*). Leaf and larvae are then sprayed with an aqueous solution or dispersion of the formulated compound to be tested. After 3 days storage at approximately 23° C., the effect of the compound is determined. At a concentration of 300 ppm (based on the content of active compound), the compound Example No. 317 cause a mortality of 90–100%.

Example In

Activity Against *Manduca sexta*

In a similar test to Example Ik(ii), using ten eggs of the tobacco homworm (*Manduca sexta*) after 7 days, at a concentration of 300 ppm (based on the content of active compound), the compounds of Example Nos. 68, 84, 100 and 116 cause 90–100% mortality.

Example Io

Activity Against *Carpocapsa pomonella* i) In a similar test to Example Ik(ii), using ten L1 larvae of the codling moth (*Carpocapsa pomonella*) after 8 days, at a concentration of 30 ppm (based on the content of active compound), the compound Example No. 76 causes a mortality of 90–100% ii) In a similar test to Example Ik(ii), using about 20 eggs of the codling moth (*Carpocapsa pomonella*), after 8 days, at a concentration of 30 ppm (based on the content of active compound), the compound of Example No. 76 causes a mortality of 90–100%.

Example Ip

Activity Against *Oncopeltus fasciatus*

Filter paper discs on which eggs of cotton stainers (*Oncopeltus fasciatus*) lie are treated with 0.5 ml of an aqueous solution or dispersion of the formulated compound to be tested. After the coating has dried on, the Petri dish is closed and the inside is kept at maximum atmospheric humidity. The dish is kept at room temperature for 7 days and the ovicidal and larvicidal action is then determined. At a concentration of 300 ppm (based on the content of active compound), the compounds of Example Nos. 68, 84, 100, 500–506, 508–511, 515–528, 530–532, 534–535 and 545, show an efficacy of 90–100%.

Example Iq

Activity Against *Diabrotica undecimpunctata* i). About 50 4–5-day-old eggs of the Southern corn rootworm (*Diabrotica undecimpunctata*) are transferred onto a filter paper which covers half the bottom of a Petri dish and which contains a germinated maize corn on a moist cotton pad. Three drops of 200 l of an aqueous solution or dispersion of the formulated compound to be tested are pipetted onto the eggs, and the rest is pipetted onto the maize corn. The Petri dish is closed and stored at about 25° C. in a controlled environment chamber. After 6 days storage, the effect of the preparation on the eggs and the larvae which may have hatched from these is determined. At a concentration of 300 ppm (based on the content of active compound), the compounds of Example Nos. 6, 39, 45, 57, 76, 94–97, 100–102, 108, 170, 224, 232, 255, 256, 263, 294, 314, 317, 320, 323, 326, 329–4, 336–8, 600–2, 701, 702, 704, 706–8, 710, 712, 713, 715, 724 and 725 cause 90–100% mortality.

ii) 1 ml of an aqueous solution or dispersion of the formulated compound to be tested is pipetted onto a filter disk. After the filter disk has dried, it is placed in a Petri dish and populated with 10 L2 larvae of the Southern corn rootworm (*Diabrotica undecimpunctata*). After 2 days in a controlled environment chamber at 26° C., the mortality is determined. At a concentration of 300 ppm (based on the content of the active compound), the compounds of Example Nos. 37, 68, 84, 100 and 116 cause a mortality of 90–100%.

Use as a Nematicide

Example Ma

Activity Against *Meloidogyne incognita*

Part A of the test (contact activity): An aqueous solution of the formulated preparation to be examined (final volume 20 ml) is added to a glass vessel containing approximately 5000 recently hatched, active (mobile) larvae (2nd development stage) of the root gall nematode (*Meloidogyne incognita*). After the nematode larvae have been permanently exposed for 6 days, the percentage of specimen which has ceased to move owing to the effect of the preparation is determined by comparison with the untreated controls (percent nematicidal contact activity).

Part B of the test (soil-drench activity): For this test, the entire solution from part A of the test (active compound and pre-treated nematode larvae) is poured into a pot filled with 60 ml of soil in which three 9-day-old cucumber plants (*Cucumis sativus*) have been planted. This drench application reduces the active compound content, based on the volume of the soil, to one third of the active compound content in part A of the test. After two weeks in a greenhouse at about 26° C. (the plants being watered twice a day), the root balls of the cucumber plants are carefully washed out from the soil mixture infested with nematodes. The number of root galls per plant is counted and compared with the infestation of untreated control plants. The reduction of infestation in percent as activity criterion is calculated using Abbott's formula (percent nematicidal soil-drench activity).

At a concentration of 3 ppm in part A of the test, compounds of Example Nos. 39, 45, 97, 100–102, 170, 224, 232, 314, 317, 320, 323, 326, 329–31, 334, 344, 535 and 600 have 90–100% activity and at 1 ppm in part B of the test, the compounds of Example Nos 39, 224, 232, 320, 330, 331, 334 and 535 have 90–100% activity.

Use as a Tickicide

Example Ta

In Vitro Test on Tropical Cattle Ticks (*Boophilus microplus*)

Ten fully satiated females of the tropical tick *Boophilus microplus* were dipped into a aqueous formulation containing 1000 ppm of the compound to tested. After five minutes, the ticks were removed and dried on filter paper and then attached by their back to an adhesive film for the purpose of oviposition. The ticks were kept in a heated cabinet at 28° C. and a relative humidity of 90%. As control, female ticks were dipped only into water. Two weeks after the treatment, the inhibition of oviposition was used to evaluate the activity. The compounds of Example Nos. 6, 39, 45, 76, 94–97, 100, 101, 102, 108, 120, 224, 232, 255, 256, 286, 330, 331, 334, 344, 501–504, 506, 508, 509, 511, 515, 518–525, 530–532, 535, 600, 601, 710–2, 715 and 721 cause 100% inhibition of oviposition.

What is claimed is:

1. A method of combating a pest which comprises applying to said pest or its locus an effective amount of a compound of the formula

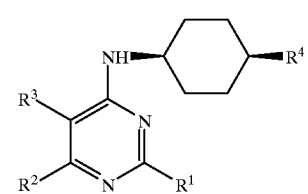

(I)

where

R$^1$ is hydrogen, chlorine, fluorine or methyl,

R$^2$ and R$^3$, which may be the same or different from each other, are hydrogen, halogen, cyano, (C$_1$–C$_4$)-alkyl, vinyl, ethynyl, (C$_1$–C$_4$)-alkoxy, (C$_1$–C$_4$)-alkoxy-(C$_1$–C$_4$)-alkyl, fluorovinyl or fluoroethyl, or R$^2$ and R$^3$ together with the linking carbon atoms form a benzo ring, and R$^4$ is (C$_2$–C$_4$)-alkyl, (C$_2$–C$_4$)-alkenyl or (C$_3$–C$_4$)-alkinyl, each of which is substituted by at least two fluorine atoms and optionally substituted by (C$_1$–C$_4$)-alkoxy, cyanomethoxy, (C$_3$–C$_4$)-alkenyloxy or (C$_3$–C$_4$)-alkynyloxy, or its acid addition salt.

2. The method according to claim 1, wherein R$^3$ is (C$_2$–C$_4$)alkyl which is substituted by at least two fluorine atoms.

3. The method according to claim 2, wherein R$^3$ is 3,3,3-trifluoropropyl or 2,2,2-trifluoro-1-methyl ethyl.

4. The method according to claim 3, wherein the compound is

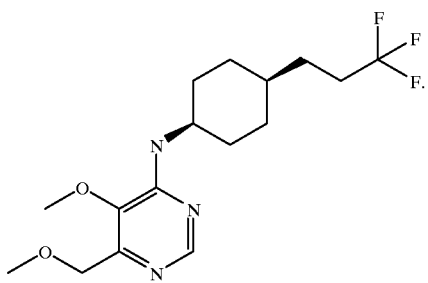

5. The method according to claim 1, wherein the pests are insects, acarides, or fungi.

6. A compound of the formula

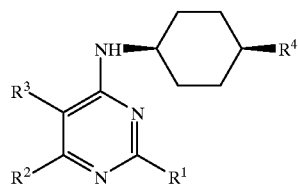

(I)

where

R¹ is hydrogen, chlorine, fluorine or methyl,

R² and R³, which may be the same or different from each other, are hydrogen, halogen, cyano, $(C_1-C_4)$-alkyl, vinyl, ethynyl, $(C_1-C_4)$-alkoxy, $(C_1-C_4)$-alkoxy-$(C_1-C_4)$-alkyl, fluorovinyl or fluoroethyl, or R² and R³ together with the linking carbon atoms form a benzo ring, and R⁴ is $(C_2-C_4)$-alkyl, $(C_2-C_4)$-alkenyl or $(C_3-C_4)$-alkinyl, each of which is substituted by at least two fluorine atoms and optionally substituted by $(C_1-C_4)$-alkoxy, cyanomethoxy, $(C_3-C_4)$-alkenyloxy or $(C_3-C_4)$-alkynyloxy, or its acid addition salt, with the proviso that R⁴ is not 3-trifluoropropyl or 2,2,2-trifluoro-1-methylethyl when R² is ethyl and R³ is chloro; and R⁴ is not 2,2,2-trifluoro-1-methylethyl when R² is methyl and R³ is chloro or bromo.

7. A compound according to claim 6, wherein R³ is $(C_2-C_4)$alkyl which is substituted by at least two fluorine atoms.

8. A compound according to claim 7, wherein R³ is 3,3,3-trifluoropropyl or 2,2,2-trifluoro-1-methyl ethyl.

9. A compound according to claim 8, which is

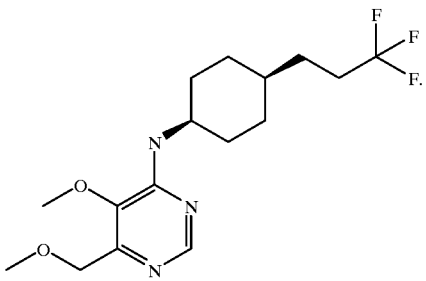

10. A pesticidal composition which comprises a compound according to claim 6 and a formulation auxiliary.

* * * * *